US009733245B2

(12) United States Patent
Kawai

(10) Patent No.: US 9,733,245 B2
(45) Date of Patent: Aug. 15, 2017

(54) CHIMERIC FC-GAMMA RECEPTOR AND METHOD FOR DETERMINATION OF ADCC ACTIVITY BY USING THE RECEPTOR

(71) Applicant: Chugai Seiyaku Kabushiki Kaisha, Tokyo (JP)

(72) Inventor: Shigeto Kawai, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 387 days.

(21) Appl. No.: 14/556,684

(22) Filed: Dec. 1, 2014

(65) Prior Publication Data

US 2015/0079610 A1 Mar. 19, 2015

Related U.S. Application Data

(62) Division of application No. 12/525,031, filed as application No. PCT/JP2008/051333 on Jan. 30, 2008, now Pat. No. 8,946,385.

(30) Foreign Application Priority Data

Jan. 30, 2007 (JP) .................. 2007-020155

(51) Int. Cl.
*G01N 33/53* (2006.01)
*G01N 33/567* (2006.01)
*G01N 33/574* (2006.01)
*G01N 33/566* (2006.01)
*C07K 14/735* (2006.01)
*C07K 16/18* (2006.01)
*G01N 33/50* (2006.01)
*C07K 1/00* (2006.01)

(52) U.S. Cl.
CPC ..... *G01N 33/566* (2013.01); *C07K 14/70535* (2013.01); *C07K 16/18* (2013.01); *G01N 33/5014* (2013.01); *C07K 2317/24* (2013.01); *C07K 2317/41* (2013.01); *C07K 2317/52* (2013.01); *C07K 2317/732* (2013.01); *C07K 2319/00* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2010/0035280 A1 2/2010 Kawai

FOREIGN PATENT DOCUMENTS

JP 2004-147565 5/2004

OTHER PUBLICATIONS

Stefanescu, R.N. et al., "Inhibitory Fc Gamma Receptors: From Gene to Disease," *J. Clin. Immunol.* 24:315-326, Plenum Publishing Corporation (2004).
Binyamin, L., et al., "Rituximab-mediated ADCC is Augmented by Concomitant Interference with Inhibitory Self-Recognition by Human NK Cells," *Proceedings of the 97th AACR Annual Meeting* 47:151, American Association for Cancer Research, Philadelphia, PA (2006).
Clemenceau, B., et al., "Antibody-dependent Cellular Cytotoxicity (ADCC) is Mediated by Genetically Modified Antigen-Specific Human T Lymphocytes," *Blood* 107: 4669-4677, The American Society of Hematology, Washington, D.C. (2006).
Cohen-Solal, J. FG., et al., "Fc γ Receptors," *Immunology Letters* 92;199-205, Elsevier B.V., Ireland (2004).
Eisenthal, A., et al., "Characterization of IL-2-Induced Marine Cells Which Exhibit ADCC Activity," *Cellular Immunology* 115;257-272, Academic Press (1988).
International Search Report for International Application No. PCT/JP2008/051333, Japanese Patent Office, Japan, mailed on Mar. 4, 2008.
Kawai, S., et al. "Antitumor Activity of Humanized Monoclonal Antibody Against HM1.24 Antigen in Human Myeloma Xenograft Models," *Oncology Reports* 15: 361-367, Spandidos Publications, Athens, Greece (2006).
Kim, M-K., et al., "Fcγ Receptor Transmembrane Domains: Role in Cell Surface Expression, γ Chain Interaction, and Phagocytosis," *Blood* 101:4479-4484, The American Society of Hematology, Washington D.C. (2003).
Lanier, L.L., et al., "Analysis of FcγRIII (CD16) Membrane Expression and Association with CD3ζ, and FceRI-γ by Site-Directed Mutation," *J. Immunol.* 146: 1571-1576, The American Association of Immunologists, Bethesda, MD (1991).
Matsuo, Y., et al.,"Immunoprofiling of Cell Lines Derived From Natural Killer-Cell and Natural Killer-Like T-Cell Leukemia-Lymphoma," *Leukemia Research* 27:935-945, Elsevier Science Ltd. (2003).
Oshima, T., et al., "Pharmacokinetics of S-1 in Patients with Peritoneal Dissemination of Gastric Cancer," *Oncology Reports* 16:361-366, Spandidos Publications, Athens, Greece (2006).

(Continued)

*Primary Examiner* — Chun Dahle
(74) *Attorney, Agent, or Firm* — Sterne, Kessler, Goldstein & Fox P.L.L.C.

(57) ABSTRACT

An objective of the present invention is to provide chimeric receptors containing a mouse Fcγ receptor extracellular domain and a human Fcγ receptor transmembrane domain, or chimeric receptors containing a mouse Fcγ receptor extracellular domain and a human γ chain transmembrane domain. Another objective of the present invention is to provide methods for measuring the ADCC activity of mouse antibodies and methods of screening for mouse antibodies having ADCC activity, using the chimeric receptors.

To accomplish the above-mentioned objectives, the present inventors produced chimeric molecules by fusing the extracellular domain of mouse FcγR3 or mouse FcγR4 with the transmembrane domain/intracellular domain of human γ chain or human FcγR3, and expressed the chimeric molecules in human NK92 cells. It was revealed that the ADCC activity can be induced by the chimeric receptors produced by any combination of the domains, and that the ADCC activity of mouse antibodies can be measured using the chimeric receptors of the present invention.

19 Claims, 7 Drawing Sheets

(56) References Cited

OTHER PUBLICATIONS

Shahied, L.S., el al., "Bispecific Minibodies Targeting HER2/neu and CD16 Exhibit Improved Tumor Lysis When Placed in a Divalent Tumor Antigen Binding Format," *J. Biol. Chem.* 279:53907-53914, The American Society for Biochemistry and Molecular Biology, Inc., Bethesda, MD (2004).

Wines, B.D., et al., "A Common Site of the Fc Receptor γ Subunit Interacts with the Unrelated Immunoreceptors FcαRI and FcεRI," *J. Biol Chem.* 281:17108-17113, The American Society for Biochemistry and Molecular Biology, Inc., Bethesda, MD (2006).

Huang, Z.-Y., et al., "The monocyte Fcγ receptors FcγRI/γ and FcγRIIA differ in their interaction with Syk and with Src-related tyrosine kinases," *Journal of Leukocyte Biology* 76:491-499, Society for Leukocyte Biology (2004).

Van den Herik-Oudijk, I.E., et al., "Functional Differences Between Two Fc Receptor ITAM Signaling Motifs," *Blood* 86:3302-3307, The American Society of Hematology (1995).

Supplementary European Search Report for European Patent Application No. 08704115.8 European Patent Office, Munich, Germany, mailed on Dec. 30, 2009.

Skolnick, J. and Fetrow, J.S., "From genes to protein structure and function: novel applications of computational approaches in the genomic era," *Trends Biotechnol* 18:34-39, Elsevier Science Ltd., England (2000).

Whisstock, J.C. and Lesk, A.M., "Prediction of protein function from protein sequence and structure," *Quarterly Review of Biophysics* 36(3):307-340, Cambridge University Press, England (2003).

CHIMERIC FC-GAMMA RECEPTOR AND METHOD FOR DETERMINATION OF ADCC ACTIVITY BY USING THE RECEPTOR

TECHNICAL FIELD

The present invention relates to chimeric Fcγ receptors of a human Fcγ receptor or the human γ chain with a mouse Fcγ receptor.

BACKGROUND ART

When developing antibody pharmaceuticals with a drug action mechanism based on antibody-dependent cell-mediated cytotoxicity (ADCC), it is important to select clones with high ADCC activity. ADCC activity is evaluated using cells expressing an antigen of interest (target cells) and effector cells that kill those target cells. Effector cells recognize the Fc region of antibodies bound to the target cells via the Fcγ receptor (FcγR). Signals transmitted from FcγR causes the effector cells to kill the target cells. FcγR binds to a molecule called the γ chain through its transmembrane domain, and transmits ADCC signals via this γ chain (Non-patent Documents 1 to 3). Mouse FcγR3 and FcγR4, and human FcγR3 are known as FcγR5 that induce ADCC. Amino acid sequence comparisons of the transmembrane domains of human and mouse FcγR5 show that five out of the 21 amino acids are different between human FcγR3 and mouse FcγR3, and seven out of the 21 amino acids are different between human FcγR3 and mouse FcγR4. Human γ chain and mouse γ chain comparisons show that one out of the 21 amino acids is different between the sequences in the transmembrane domains (Non-patent Document 4).

When measuring the ADCC activity of human antibodies, human NK cells are used as effector cells. Human NK cells can be purified from human peripheral blood mononuclear cells (PBMC) using the NK Cell Isolation Kit II (Miltenyi Biotec K.K.). Alternatively, PBMC can be used directly as effector cells. PBMC can be purchased (from Cambrex Corporation), or can be prepared from fresh peripheral blood collected from volunteers. However, when such cells are used as effector cells, the drawbacks include lot-to-lot differences and laborious preparation.

To avoid such drawbacks, systems that use human NK cell lines as effector cells have been developed for measuring the ADCC activity of human antibodies. The NK92 human NK cell line (ATCC) does not express human FcγR, but expresses the human γ chain (Non-patent Document 5). Therefore, ADCC activity can be induced by forcedly-expressing human FcγR3 in the NK92 human NK cell line (Non-patent Documents 6 and 7). This greatly reduced preparation labor and enabled accurate measurements having small lot-to-lot differences. Furthermore, it has been reported that chimeric molecules produced by fusing the extracellular domain of human FcγR3 and the transmembrane domain and intracellular domain of human γ chain induce ADCC activity related to human antibodies (Non-patent Document 8).

On the other hand, when measuring the ADCC activity of mouse antibodies, mouse spleen cells are used as effector cells (Non-patent Documents 9 and 10). To prepare mouse spleen cells, it is necessary to remove the spleen from mice, hemolyze erythrocytes, and activate NK cells with interleukin 2. However, since spleen cells prepared in this manner have high natural killer activity to kill target cells in an antibody-independent manner, the ADCC activity may not be measurable depending on the type of target cells. Furthermore, preparation of the effector cells requires effort.

Systems for measuring the ADCC activity of human antibodies using human NK cell lines have been developed. However, since the use of mouse NK cell lines is generally unknown, a system for conveniently measuring the ADCC activity of mouse antibodies using an NK cell line has not been established. Furthermore, since there are sequence differences between Fcγ receptors and γ chains between human and mouse, even if mouse FcγR is expressed as it is in human NK92 cells, mouse FcγR will not be able to bind to the human γ chain with similar strength as human FcγR.

Therefore, to measure the ADCC activity of mouse antibodies, it was necessary to use a method that requires much effort such as the method of preparing mouse spleen cells as described above, or the method of preparing a chimeric antibody in which the antibody Fc regions have been replaced with those of a human antibody.

Prior art literature information relating to the present invention is shown below.
[Non-patent Document 1] Blood 2003, 101, 4479.
[Non-patent Document 2] J. Immunol. 1991, 146, 1571
[Non-patent Document 3] Immunol. Lett. 2004, 92, 199
[Non-patent Document 4] J. Biol. Chem. 2006, 281, 17108
[Non-patent Document 5] Leukemia Res. 2003, 27, 935
[Non-patent Document 6] 97th AACR annual meeting 2006, abstract number 635
[Non-patent Document 7] J. Biol. Chem. 2004, 279, 53907
[Non-patent Document 8] Blood 2006, 107, 4669
[Non-patent Document 9] Oncol. Rep. 2006, 15, 361
[Non-patent Document 10] Cell. Immunol. 1988, 115, 257

DISCLOSURE OF THE INVENTION

Problems to be Solved by the Invention

An objective of the present invention is to provide chimeric receptors comprising a mouse Fcγ receptor extracellular domain and a human Fcγ receptor transmembrane domain, and chimeric receptors comprising a mouse Fcγ receptor extracellular domain and a human γ chain transmembrane domain. Another objective of the present invention is to provide methods for measuring the ADCC activity of mouse antibodies using the chimeric receptors. A further objective of the present invention is to provide methods of screening for mouse antibodies having ADCC activity using the chimeric receptors.

Means for Solving the Problems

To achieve the above-mentioned objectives, the present inventors produced chimeric molecules by fusing the extracellular domain of mouse FcγR3 or mouse FcγR4 with the transmembrane domain and intracellular domain of human γ chain or human FcγR3, and expressed the chimeric molecules in human NK92 cells. The present inventors found that any one of the combinations of mouse FcγR3 and human γ chain, mouse FcγR3 and human FcγR3, mouse FcγR4 and human γ chain, and mouse FcγR4 and human FcγR3 can induce the ADCC activity. Thus, the present inventors discovered that the ADCC activity of mouse antibodies can be measured by using a chimeric receptor produced from a mouse Fcγ receptor and a human Fcγ receptor, or a chimeric receptor produced from a mouse Fcγ receptor and the human γ chain. Furthermore, the present inventors discovered that mouse antibodies having ADCC activity can be screened for by using a chimeric receptor produced from a mouse Fcγ receptor and a human Fcγ receptor, or produced from a mouse Fcγ receptor and the human γ chain.

Specifically, the present application provides the following:
[1] a chimeric protein comprising a mouse Fcγ receptor extracellular domain and a human γ chain transmembrane domain;
[2] the chimeric protein of [1], wherein the chimeric protein further comprises a human γ chain intracellular domain;
[3] a chimeric protein comprising a mouse Fcγ receptor extracellular domain and a human Fcγ receptor transmembrane domain;
[4] the chimeric protein of [3], wherein the chimeric protein further comprises a human Fcγ receptor intracellular domain;
[5] the chimeric protein of [3] or [4], wherein the human Fcγ receptor is human Fcγ receptor 3;
[6] the chimeric protein of any one of [1] to [5], wherein the mouse Fcγ receptor is mouse Fcγ receptor 3;
[7] the chimeric protein of any one of [1] to [5], wherein the mouse Fcγ receptor is mouse Fcγ receptor 4;
[8] a gene encoding the chimeric protein of any one of [1] to [7];
[9] a vector comprising the gene of [8];
[10] a cell expressing the chimeric protein of any one of [1] to [7];
[11] the cell of [10], wherein the cell is an NK cell;
[12] the cell of [10] or [11], wherein the cell is a human-derived cell;
[13] a method for measuring the cytotoxic activity of an antibody, wherein the method comprises the steps of:
 (a) contacting a test antibody with a cell expressing an antigen to which the test antibody binds;
 (b) contacting the test antibody of (a) with the cell of any one of [10] to [12]; and
 (c) measuring the cytotoxic activity of the test antibody;
[14] the measurement method of [13], wherein the test antibody is a mouse-derived antibody;
[15] a method of screening for an antibody having cytotoxic activity, wherein the method comprises the steps of:
 (a) contacting a test antibody with a cell expressing an antigen to which the test antibody binds;
 (b) contacting the test antibody of (a) with the cell of any one of [10] to [12];
 (c) measuring the cytotoxic activity of the test antibody; and
 (d) selecting an antibody having cytotoxic activity;
[16] the screening method of [15], wherein the test antibody is a mouse-derived antibody;
[17] use of the chimeric protein of any one of [1] to [7] for measuring cytotoxic activity;
[18] use of the cell of any one of [10] to [12] for measuring cytotoxic activity;
[19] use of the chimeric protein of any one of [1] to [7] for screening for an antibody having cytotoxic activity;
[20] use of the cell of any one of [10] to [12] for screening for an antibody having cytotoxic activity.

MODE FOR CARRYING OUT THE INVENTION

The present invention provides chimeric receptors comprising a mouse Fcγ receptor extracellular domain and a human Fcγ receptor transmembrane domain. The present invention also provides chimeric receptors comprising a mouse Fcγ receptor extracellular domain and a human γ chain transmembrane domain.

The chimeric receptors of the present invention are preferably receptors that exhibit the activity to transmit signals into cells when the Fc region of a mouse antibody is bound to the extracellular domain of the receptors.

The mouse Fcγ receptors used in the present invention are not particularly limited, and any mouse Fcγ receptor may be used. The receptors are preferably mouse Fcγ receptor 3 (FcγR3) and mouse Fcγ receptor 4 (FcγR4).

Comparing the expression pattern of mouse FcγR3 and mouse FcγR4, mouse FcγR3 is expressed mainly in NK cells, and mouse FcγR4 is expressed in macrophages and neutrophils (Immunity 2005, 23, 41). Mouse FcγR3 binds to mouse IgG1, mouse IgG2a, and mouse IgG2b, while mouse FcγR4 does not bind to mouse IgG1 (Immunity 2005, 23, 41; Science 2005, 310, 1510). Therefore, when evaluating the ADCC activity of various types of mouse antibodies, mouse FcγR3, which allows measurement using even mouse IgG1, is preferably used.

Known nucleotide sequences of the DNAs encoding mouse Fcγ receptors, and known amino acid sequences thereof can be used. For example, as the nucleotide sequences of DNAs encoding mouse Fcγ receptor 3 and mouse Fcγ receptor 4, and the amino acid sequences thereof, the sequences of SEQ ID NO: 1 (mouse Fcγ receptor 3 nucleotide sequence), SEQ ID NO: 2 (mouse Fcγ receptor 3 amino acid sequence), SEQ ID NO: 3 (mouse Fcγ receptor 4 nucleotide sequence), and SEQ ID NO: 4 (mouse Fcγ receptor 4 amino acid sequence) may be used. Within the amino acid sequence of SEQ ID NO: 2, amino acid positions 31 to 212 correspond to the extracellular domain of mouse Fcγ receptor 3. Within the amino acid sequence of SEQ ID NO: 4, amino acid positions 19 to 201 correspond to the extracellular domain of mouse Fcγ receptor 4.

The extracellular domain of a receptor may be the entire extracellular domain, or may be a portion thereof. The entire extracellular domain is preferably used, since the receptor activity, such as the activity to bind to an antibody Fc region, can be appropriately retained. When using a portion of the extracellular domain of a receptor, the portion preferably retains the activity to bind to an antibody Fc region. The mouse Fcγ receptor extracellular domain used for the chimeric receptors of the present invention may include amino acid substitutions, deletions, insertions, and/or additions, as long as the domains have the ability to bind to an antibody Fc region. A method of introducing mutations into a protein is well-known to those skilled in the art as a method for preparing proteins that are functionally equivalent to a certain protein. For example, those skilled in the art can prepare such proteins using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. The number of mutated amino acids in such mutants is generally 50 amino acids or less, preferably 30 amino acids or less, more preferably 20 amino acids or less, still more preferably ten amino acids or less, and yet more preferably five amino acids or less.

It is desirable that the amino acid residues are mutated into other amino acids in which the properties of the amino acid side chains are conserved. For example, amino acids are categorized as follows depending on the side chain properties: hydrophobic amino acids (A, I, L, M, F, P, W, Y, and V); hydrophilic amino acids (R, D, N, C, E, Q, G, H, K, S, and T); amino acids having aliphatic side chains (G, A, V, L, I, and P); amino acids having hydroxyl-containing side chains (S, T, and Y); amino acids having sulfur atom-containing side chains (C and M); amino acids having carboxylic acid- and amide-containing side chains (D, N, E, and Q); amino acids having base-containing side chains (R, K, and H); and amino acids having aromatic ring-containing side chains (H, F, Y, and W) (amino acids are represented by one-letter codes in parentheses).

Polypeptides having a modified amino acid sequence, in which one or more amino acid residues in a certain amino acid sequence is deleted, added, and/or substituted with other amino acids, are known to retain the biological activity of the original polypeptides (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

The mouse Fcγ receptor extracellular domain used for the chimeric receptors of the present invention may be a polypeptide having high homology to a mouse Fcγ receptor (for example, mouse Fcγ receptor 3, mouse Fcγ receptor 4, etc.), as long as the polypeptide has the ability to bind to an antibody Fc region. In the present invention, "high homology" of a polypeptide generally refers to a sequence identity of 70% or higher, preferably 80% or higher, more preferably 90% or higher, and still more preferably 95% or higher. Polypeptide homology can be determined by the algorithm described in literature (Wilbur, W. J. and Lipman, D. J. Proc. Natl. Acad. Sci. USA (1983) 80, 726-730).

To isolate a DNA encoding a polypeptide having high homology to a mouse Fcγ receptor, hybridization reaction may be usually performed under stringent conditions. Stringent hybridization conditions can be selected appropriately by those skilled in the art. For example, hybridization may be performed by conducting overnight prehybridization at 42° C. in a hybridization solution containing 25% formamide, or 50% formamide under more stringent conditions; 4×SSC; 50 mM Hepes pH 7.0; 10×Denhardt's solution; and 20 µg/mL denatured salmon sperm DNA, then adding a labeled probe, and then incubating the solution overnight at 42° C. The subsequent washing can be carried out using washing solution and temperature conditions of "1×SSC, 0.1% SDS, 37° C." or such, "0.5×SSC, 0.1% SDS, 42° C." or such for more stringent conditions, or "0.2×SSC, 0.1% SDS, 65° C." or such for even more stringent conditions. The more stringent the washing conditions for hybridization are, the higher the homology of an isolated DNA to the probe sequence is expected to be. However, the above-mentioned combinations of SSC, SDS, and temperature conditions are examples, and those skilled in the art can suitably combine the above-mentioned factors and/or other factors (for example, probe concentration, probe length, hybridization reaction time, etc.) that determine hybridization stringency, to realize similar stringency.

The homology of a DNA isolated is at least 50% or more, more preferably 70% or more, and even more preferably 90% or more (for example, 95%, 96%, 97%, 98%, 99%, or more), in terms of overall amino acid sequence identity. Programs such as BLASTN (nucleic acid level) and BLASTX (amino acid level) (Altschul et al. J. Mol. Biol., 215:403-410, 1990) can be used to determine the sequence homology. These programs are based on the BLAST algorithm by Karlin and Altschul (Proc. Natl. Acad. Sci. USA, 87:2264-2268, 1990; Proc. Natl. Acad. Sci. USA, 90: 5873-5877, 1993). When nucleotide sequences are analyzed by BLASTN, parameters are set, for example, at score=100 and wordlength=12. When amino acid sequences are analyzed by BLASTX, parameters are set, for example, at score=50 and wordlength=3. When amino acid sequences are analyzed using the Gapped BLAST program, the analysis can be performed as described by Altschul et al. (Nucleic Acids Res. 25: 3389-3402, 1997). When using the BLAST and Gapped BLAST programs, the default parameters of each program are utilized. Specific procedures for these analytical methods are known.

Alternatively, a DNA encoding a polypeptide highly homologous to a mouse Fcγ receptor can be isolated by utilizing a gene amplification method such as polymerase chain reaction (PCR) using primers that are synthesized based on the sequence information of DNAs encoding mouse Fcγ receptors (SEQ ID NOs: 1 and 3).

In the chimeric receptors of the present invention, a human Fcγ receptor transmembrane domain or a human γ chain transmembrane domain is used as the transmembrane domain.

The human Fcγ receptor used in the present invention is not particularly limited and may be any human Fcγ receptor; however, human Fcγ receptor 3 is preferred. Known nucleotide sequences of the DNAs encoding human Fcγ receptors, and known amino acid sequences thereof can be used. For example, as the nucleotide sequence of the DNA encoding human Fcγ receptor 3 and the amino acid sequence thereof, the sequences of SEQ ID NO: 5 (human Fcγ receptor 3 nucleotide sequence) and SEQ ID NO: 6 (human Fcγ receptor 3 amino acid sequence) may be used. Within the amino acid sequence of SEQ ID NO: 6, amino acid positions 207 to 229 correspond to the transmembrane domain.

Furthermore, the nucleotide sequence of the DNA encoding the human γ chain and the amino acid sequence thereof are known. For example, the sequences of SEQ ID NO: 7 (human γ chain nucleotide sequence) and SEQ ID NO: 8 (human γ chain amino acid sequence) can be used. In the amino acid sequence of SEQ ID NO: 8, amino acid positions 24 to 44 correspond to the transmembrane domain.

The transmembrane domain of a receptor may be the entire transmembrane domain or may be a portion thereof. The entire transmembrane domain is preferably used, since receptor activity such as signal transduction activity can be appropriately retained. When using a portion of the transmembrane domain, the portion preferably retains the signal transduction activity. The transmembrane domain used for the chimeric receptors of the present invention may include amino acid substitutions, deletions, insertions, and/or additions. The transmembrane domain used in the present invention may be a polypeptide highly homologous to such a transmembrane domain. Amino acid substitutions, deletions, insertions, and additions, and highly homologous polypeptides are as described above. Polypeptides with amino acid substitutions, deletions, insertions, and/or additions, and highly homologous polypeptides preferably retain the signal transduction activity of the transmembrane domain.

Preferably, chimeric receptors of the present invention, which comprise a mouse Fcγ receptor extracellular domain and a human Fcγ receptor transmembrane domain, or comprise a mouse Fcγ receptor extracellular domain and a human γ chain transmembrane domain, further comprise an intracellular domain.

An intracellular domain used for the chimeric receptors of the present invention is not particularly limited, and may be any type of intracellular domain. When a human Fcγ receptor transmembrane domain is used as the transmembrane domain, a human Fcγ receptor intracellular domain is preferably used as the intracellular domain. When the human γ chain is used as the transmembrane domain, a human γ chain intracellular domain is preferably used as the intracellular domain.

As the human Fcγ receptor 3 intracellular domain, for example, the region of amino acid positions 230 to 254 in the amino acid sequence of SEQ ID NO: 6 can be used. As the human γ chain intracellular domain, for example, the region of amino acid positions 45 to 86 in the amino acid sequence of SEQ ID NO: 8 can be used.

The intracellular domain of a receptor may be the entire intracellular domain, or may be a portion thereof. The entire intracellular domain is preferably used, since the receptor activity such as signal transduction activity can be appropriately retained. When using a portion of the intracellular domain, the portion preferably retains the signal transduction activity. The intracellular domain used for the chimeric receptors of the present invention may comprise amino acid substitutions, deletions, insertions, and additions. The intracellular domain used in the present invention may be a polypeptide highly homologous to such an intracellular domain. Amino acid substitutions, deletions, insertions, and additions, and highly homologous polypeptides are as described above. Polypeptides with amino acid substitutions, deletions, insertions, and/or additions, and highly homologous polypeptides preferably retain the signal transduction activity of the intracellular domain.

In a preferred embodiment, the chimeric receptors of the present invention include the chimeric receptors of (a) to (f) below:

(a) a chimeric receptor comprising the amino acid sequence of SEQ ID NO: 10 (a chimeric receptor comprising the mouse FcγR3 extracellular domain and the human FcγR3 transmembrane domain and intracellular domain; "mouse FcγR3/human FcγR3");

(b) a chimeric receptor comprising the amino acid sequence of SEQ ID NO: 12 (a chimeric receptor comprising the mouse FcγR3 extracellular domain and the human γ chain transmembrane domain and intracellular domain; "mouse FcγR3/human γ chain");

(c) a chimeric receptor comprising the amino acid sequence of SEQ ID NO: 14 (a chimeric receptor comprising the mouse FcγR4 extracellular domain and the human FcγR3 transmembrane domain and intracellular domain; "mouse FcγR4/human FcγR3");

(d) a chimeric receptor comprising the amino acid sequence of SEQ ID NO: 16 (a chimeric receptor comprising the mouse FcγR4 extracellular domain and the human γ chain transmembrane domain and intracellular domain; "mouse FcγR4/human γ chain);

(e) receptors in which one or more amino acids are substituted, deleted, added, and/or inserted in the chimeric receptors of (a) to (d) above, which are chimeric receptors having activity equivalent to that of the chimeric receptors of (a) to (d).

(f) receptors having amino acid sequences that are highly homologous to the amino acid sequences of the chimeric receptors of (a) to (d) above, which are chimeric receptors having activity equivalent to that of the chimeric receptors of (a) to (d).

Amino acid substitutions, deletions, additions, and insertions, and high homology are as described above.

In the present invention, "having 'activity equivalent to' that of the chimeric receptors of (a) to (d)" refers to having equivalent biological or biochemical activity. Examples of the biological or biochemical activity of the chimeric receptors of the present invention include the ability to bind to the Fc region of a mouse antibody or the ability to transmit ADCC signals.

The activity of the chimeric receptors of the present invention to bind to a mouse antibody Fc region can be measured by methods known to those skilled in the art, such as the ELISA, BIACORE, and Western blotting methods.

Whether or not the chimeric receptors of the present invention transmit ADCC signals can be determined by methods known to those skilled in the art. For example, it can be determined by using a chimeric receptor-expressing human NK cells (human NK92 cells or such) as effector cells, contacting the NK cells with a mouse antibody bound to an antigen expressed on target cells, and measuring the ADCC activity. More specifically, it can be determined by the methods described below, or by the methods described in the Examples of the present invention.

DNAs encoding the chimeric receptors of the present invention, and transcriptional RNA products of the DNAs are also included in the present invention. The DNAs encoding the chimeric receptors of the present invention can be prepared by methods known to those skilled in the art. For example, DNAs encoding the extracellular domain and the transmembrane domain can be prepared by making a cDNA library from cells expressing a receptor from which the extracellular domain or the transmembrane domain of the present invention is derived, and then performing hybridization using a portion of a known DNA sequence as the probe. DNAs encoding the chimeric receptors of the present invention can be prepared by linking the respective DNAs prepared.

Examples of the nucleotide sequences of the DNAs encoding the chimeric receptors of the present invention include the nucleotide sequences of SEQ ID NO: 9 (mouse FcγR3/human FcγR3), SEQ ID NO: 11 (mouse FcγR3/human γ chain), SEQ ID NO: 13 (mouse FcγR4/human FcγR3), and SEQ ID NO: 15 (mouse FcγR4/human γ chain).

The prepared DNA encoding a chimeric receptor of the present invention is ligated to a vector DNA. A recombinant vector is thus produced, then introduced into *Escherichia coli* or such, a colony is selected, and a desired recombinant vector can be prepared. As the vector DNA for carrying a DNA, known vector DNAs (for example, pUC19 and pBluescript) can be used. Known *E. coli* strains (for example, DH5α, and JM109) may be used. The nucleotide sequence of a DNA of interest can be identified by a known method, such as dideoxynucleotide chain termination. Alternatively, an automatic sequencing apparatus can be used.

DNAs of the present invention may be designed to have nucleotide sequences that are expressed more efficiently considering the codon usage frequency in the host used for expression (Grantham R. et al. Nucleic Acids Res. (1981)9, r43-74). DNAs of the present invention can be modified by commercially available kits or known methods. Examples of the modification include digestion with restriction enzymes, insertion of a synthetic oligonucleotide or an appropriate DNA fragment, addition of a linker, and insertion of the initiation codon and/or a stop codon.

A chimeric receptor of the present invention can be expressed by producing an expression vector comprising a DNA encoding the chimeric receptor linked to an expression regulatory region such as a promoter. This expression vector is used to transform a host cell to express the chimeric receptor in the cell. Enhancers or such may be included in the vector.

Promoters that are useful for expression in host cells include virus promoters such as cytomegalovirus, retrovirus, polyomavirus, adenovirus, and SV40 promoters, and promoters derived from mammalian cells.

Selection marker genes can be included in the expression vectors for gene transfer into host cells.

Gene transfer into host cells can be carried out by known methods such as the calcium phosphate method, the lipofection method, and the electroporation method.

The present invention provides vectors comprising a DNA encoding a chimeric receptor of the present invention. Vectors used in the present invention are not particularly limited, and may be any vector. A vector can be appropriately selected by those skilled in the art. For example, pCOS1 (WO98/13388), pME18S (Med. Immunol. 20, 27-32 (1990)), pEF-BOS (Nucleic Acids Res. 18, 5322 (1990)), pCDM8 (Nature 329, 840-842 (1987)), pRSV-neo, pcDNAI/Amp (Invitrogen), pcDNAI, pAMoERC3Sc, pCDM8 (Nature 329, 840 (1987)), pAGE107 (Cytotechnology 3, 133 (1990)), pREP4 (Invitrogen), pAGE103 (J. Biochem. 101, 1307 (1987)), pAMoA, pAS3-3, pCAGGS (Gene 108, 193-200 (1991)), pBK-CMV, pcDNA3.1 (Invitrogen), pZeoSV (Stratagene), and such may be used.

The present invention relates to cells expressing a chimeric receptor of the present invention. Cells expressing a chimeric receptor of the present invention can be produced by methods known to those skilled in the art. For example, the cells can be produced by introducing the above-mentioned vectors of the present invention into the cells. Cells used in the present invention are not particularly limited, and may be of any type. However, the cells are preferably effector cells, more preferably NK cells, and particularly preferably NK92 cells. Cells used in the present invention are preferably human-derived cells. In particular, human-derived NK cells are preferred. Known human NK cells may be used, or human NK cells may be produced and used. Cells used in the present invention may be cells expressing the human γ chain, or cells that do not express the human γ chain. However, cells expressing the human γ chain are preferred. When using cells that do not express the human γ chain or cells with low expression level of the human γ chain, expression of the human γ chain can be forced by introducing a gene encoding the human γ chain.

The present invention provides methods of measuring the cytotoxic activity of antibodies using a chimeric receptor of the present invention.

The cytotoxic activity can be measured using a chimeric receptor of the present invention in a manner similar to conventional cytotoxic activity measurements.

For example, the measurements can be performed by methods comprising the steps of:
(a) contacting a test antibody with a cell expressing an antigen to which the test antibody binds;
(b) contacting the test antibody of (a) with a cell expressing a chimeric receptor of the present invention; and
(c) measuring the cytotoxic activity of the test antibody.

In the present invention, "measurements" include quantitative and qualitative measurements. Examples of qualitative measurements include, for example, measurement only for the presence or absence of cytotoxic activity in a test antibody, measurement to see whether or not a test antibody has cytotoxic activity above a certain level, and measurement that compares the cytotoxic activity of a test antibody with that of control antibodies (positive control, negative control, etc.). On the other hand, examples of quantitative detection include measurement of the absolute or relative value of the cytotoxic activity of a test antibody, and evaluation of the usefulness of a test antibody as a pharmaceutical.

The present invention also provides methods of screening for an antibody having cytotoxic activity, which use a chimeric receptor of the present invention.

Specifically, screening for an antibody having cytotoxic activity can be performed by methods comprising the steps of:
(a) contacting a test antibody with a cell expressing an antigen to which the test antibody binds;
(b) contacting the test antibody of (a) with a cell expressing a chimeric receptor of the present invention;
(c) measuring the cytotoxic activity of the test antibody; and
(d) selecting an antibody having cytotoxic activity.

The screening methods of the present invention may be any method including screening for antibodies having cytotoxic activity from test antibodies for which the presence or absence of cytotoxic activity is unknown; screening for antibodies having high cytotoxic activity from test antibodies having cytotoxic activity; and screening for antibodies that are useful as pharmaceuticals from test antibodies having cytotoxic activity, or from test antibodies for which the presence or absence of the cytotoxic activity is unknown.

In the methods of the present invention, the cytotoxic activity measured is generally antibody-dependent cell-mediated cytotoxicity (ADCC activity).

The test antibodies used in the methods of the present invention are not particularly limited. While any type of antibody may be used, the test antibodies generally have a region that can bind to the extracellular domain of a chimeric receptor of the present invention. Preferred examples of the test antibodies include mouse antibodies, and antibodies having an Fc region derived from a mouse antibody. The amino acid sequence of an Fc region of the test antibodies can be modified, and so can the sugar chain(s).

Antigens to which the test antibodies bind are not particularly limited, but are preferably membrane proteins. Examples of membrane proteins include receptors, transport proteins, ion channels, and cell membrane antigens.

In the present invention, preferred examples of antigens to which the test antibodies bind include disease-related antigens. Disease-related antigens are antigens that have been demonstrated to be expressed in a specific disease, and are preferably antigens whose expression level increases under a specific disease state compared to normal conditions. Examples of disease-related antigens include proteins highly expressed in cancers, and proteins highly expressed in autoimmune diseases.

A cell expressing the antigen can be any cell, and may be a cell that inherently expresses the antigen to which a test antibody binds, or a cell in which expression of the antigen is forced by introducing a gene encoding the antigen. Preferred examples of antigens used in the methods of the present invention include cancer cells, or autoimmune disease-related cells such as B cells.

Generally, in the methods of the present invention, a test antibody is contacted with a cell expressing an antigen to which the test antibody binds, and then the test antibody bound to the cell expressing the antigen is contacted with a cell expressing a chimeric receptor of the present invention. However, the order in which the test antibody, the cell expressing the antigen, and the cell expressing the chimeric receptor of the present invention are contacted is not limited to the above-described order. The test antibody, the cell expressing the antigen, and the cell expressing the chimeric receptor of the present invention may be contacted simultaneously. Alternatively, after contacting the test antibody with the cell expressing the chimeric receptor of the present invention, the cell expressing the antigen may be contacted with them.

Whether or not an antibody has ADCC activity can be determined by known methods (for example, Current Protocols in Immunology, Chapter 7. Immunologic studies in humans, Editor, John E, Coligan et al., John Wiley & Sons, Inc., (1993)).

Specifically, the determination can be carried out by the following method.

First, effector cells and target cells are prepared.

(1) Preparation of Effector Cells

The effector cells can be prepared by adjusting the concentration of chimeric receptor-expressing cells of the present invention to $5 \times 10^6$ cells/mL.

(2) Preparation of Target Cells

The target cells can be radioactively labeled by incubating cells expressing an antigen to which a test antibody binds with 0.2 mCi of sodium chromate-$^{51}$Cr (manufactured by GE Healthcare Bio-Sciences) in RPMI 1640 medium containing 10% FBS for one hour at 37° C. After radioactive labeling, cells are washed three times in RPMI 1640 medium containing 10% FBS. The target cells can be prepared by adjusting the cell concentration to $2 \times 10^5$ cells/mL.

The intensity of ADCC activity can be measured by the method described below. Fifty μL each of the target cells and the test antibody are added to a 96-well U-bottomed plate manufactured by Becton Dickinson), and reacted for 15 minutes on ice. Thereafter, 100 μL of the cells expressing a chimeric receptor of the present invention are added as the effector cells, and incubated in a carbon dioxide gas incubator for four hours. The final concentration of the antibody is adjusted to 0 or 10 μg/mL. After incubation, 100 μL of the supernatant is collected, and the radioactivity is measured by a gamma counter (COBRAII AUTO-GAMMA, MODEL D5005, manufactured by Packard Instrument Company). Using the values obtained, the cytotoxic activity (%) can be calculated according to the equation: $(A-C)/(B-C) \times 100$, wherein A represents the radioactivity (cpm) in each sample, B represents the radioactivity (cpm) in a sample to which 1% NP-40 (manufactured by Nacalai Tesque) has been added, and C represents the radioactivity (cpm) of a sample containing only the target cells.

The antibodies having cytotoxic activity that are selected by the screening methods of the present invention can be used as pharmaceuticals for treating or preventing various types of diseases. For example, the antibodies may be used as therapeutic agents or preventive agents against diseases such as cancers or autoimmune diseases.

The present invention further provides methods of producing antibodies having cytotoxic activity, which use the chimeric receptors of the present invention. Specifically, the production can be carried out by methods comprising the steps of:

(a) contacting a test antibody with a cell expressing an antigen to which the test antibody binds;
(b) contacting the test antibody of (a) with a cell expressing a chimeric receptor of the present invention;
(c) measuring the cytotoxic activity of the test antibody;
(d) selecting an antibody having cytotoxic activity;
(e) producing an expression vector comprising a gene encoding the antibody selected;
(f) transfecting the vector of (e) into host cells;
(g) culturing the host cells of (f); and
(h) collecting the antibody from the host cells cultured in (g).

The gene encoding the selected antibody may be a gene encoding an antibody having an amino acid sequence that is identical to the full amino acid sequence of the selected antibody, or a gene encoding an antibody having an amino acid sequence partially identical to that of the selected antibody. Preferred examples of an antibody having an amino acid sequence partially identical to that of the selected antibody include antibodies having variable regions identical to those of the selected antibody, and antibodies having complementarity determining regions (CDRs) identical to those of the selected antibody. Methods for substituting regions other than variable regions or CDRs with sequences derived from other antibodies are known (see, European Patent Publication No. EP 239,400, and International Patent Publication No. WO 96/02576).

When using these antibodies as pharmaceuticals for humans or mammals, besides administering them directly as they are to patients, they can be administered as formulations produced by known preparation methods. For example, as necessary, the antibodies may be administered orally as tablets, capsules, or such; or parenterally in the form of injections of sterile solutions or suspensions prepared with water or other pharmaceutically acceptable liquids. For example, the antibodies may be formulated by appropriately combining them with pharmaceutically acceptable carriers or media, more specifically, sterilized water or physiological saline solutions, vegetable oils, emulsifiers, suspending agents, surfactants, stabilizers, flavoring agents, vehicles, preservatives, binding agents, and such, and mixing them into a unit dosage form required for generally accepted pharmaceutical practice. The amount of active ingredient in the formulation is such that appropriate doses within indicated ranges are achieved. Additives that can be mixed into tablets and capsules include, for example, binding agents such as gelatin, cornstarch, tragacanth gum, and gum arabic; excipients such as crystalline cellulose; swelling agents such as cornstarch, gelatin, alginic acid; lubricants such as magnesium stearate; sweeteners such as sucrose, lactose, and saccharine; and flavoring agents such as peppermint and *Gaultheria adenothrix* oils, and cherry. When the unit dosage form is a capsule, liquid carriers such as oils and fats can be further included in the above-indicated materials. Sterile compositions to be injected can be formulated using a vehicle such as distilled water for injection, according to standard formulation practice.

Aqueous solutions for injections include, for example, physiological saline and isotonic solutions containing glucose or other adjunctive agents such as D-sorbitol, D-mannose, D-mannitol, and sodium chloride. The solutions may also be combined with appropriate solubilizing agents such as alcohol, more specifically, ethanol, polyalcohol such as propylene glycol or polyethylene glycol, or non-ionic surfactants such as Polysorbate 80 or HCO-50.

Oil solutions include sesame oils and soybean oils, and can be combined with solubilizing agents such as benzyl benzoate or benzyl alcohol. Injection solutions may also be formulated with buffers such as phosphate buffers or sodium acetate buffers; analgesics such as procaine hydrochloride; stabilizers such as benzyl alcohol or phenol; or anti-oxidants. The solutions prepared are typically aliquoted into appropriate ampules.

Administration to patients may be performed, for example, by intra-arterial injection, intravenous injection, or subcutaneous injection, alternatively, by intranasal, transbronchial, intramuscular, transdermal, or oral administration, using methods known to those skilled in the art.

All prior art references cited herein are incorporated by reference into this description.

EXAMPLES

Figure 1:
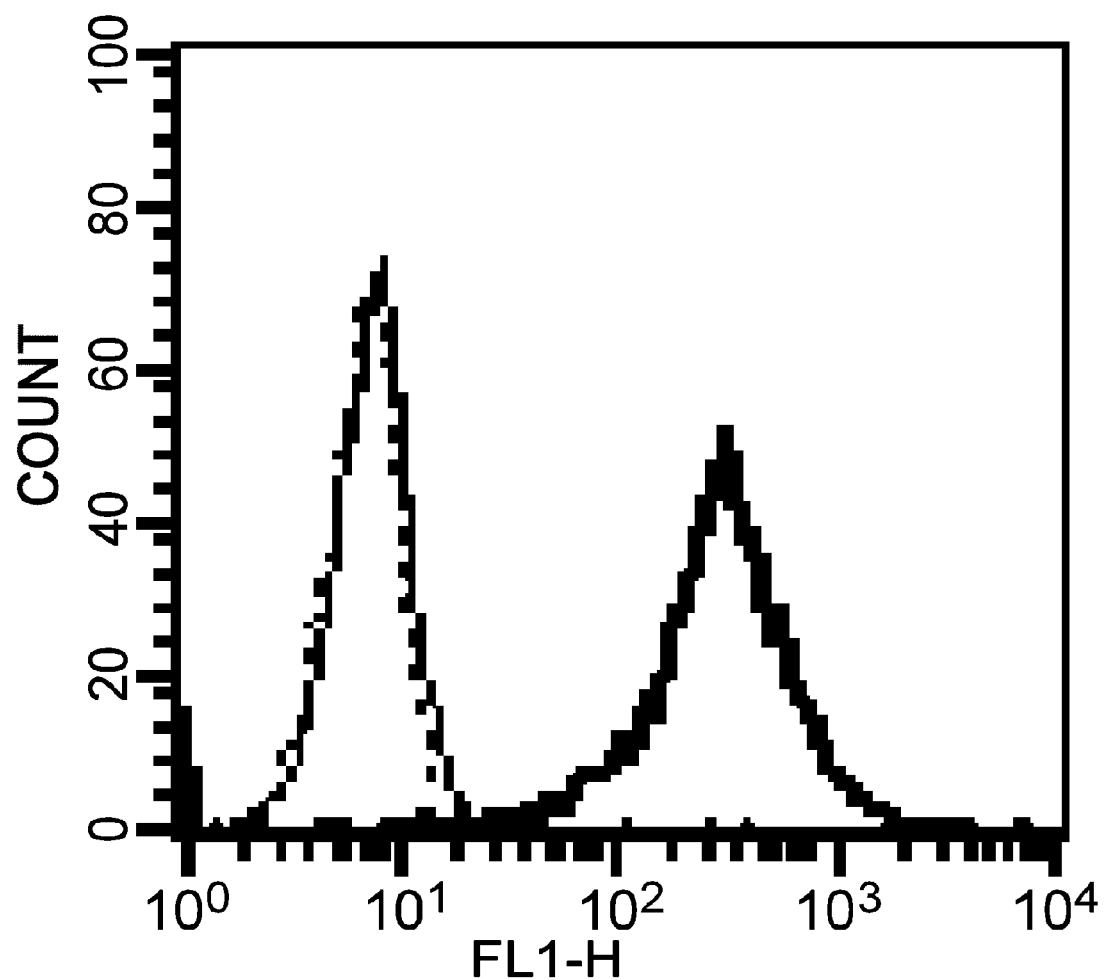
FIG. 1 shows the results of measuring DSG3 expression in DSG3-Ba/F3 cells by flow cytometry. The results are indicated by a thick line for DSG3 monoclonal antibody (R&D Systems), a solid line for the negative control antibody (mouse IgG2a, Becton Dickinson), and a dashed line for no primary antibody.

Herein below, the present invention will be specifically described with reference to the Examples, but it is not to be construed as being limited thereto.

Example 1

Establishment of FcγR-Expressing NK92 Cell Lines 1-1) Construction of Mouse FcγR4 Expression Vector Using mouse spleen cDNA (Clontech) as a template, the mouse FcγR4 gene was amplified by PCR utilizing a sense primer containing an EcoRI restriction enzyme sequence (mFcR4-EcoRI-F, SEQ ID NO: 17) and an antisense primer containing a NotI restriction enzyme sequence (mFcR4-NotI-R, SEQ ID NO: 18). After treatment with the EcoRI and NotI restriction enzymes, the amplified product was cloned into the EcoRI-NotI site of the pMCDN plasmid for expression in mammalian cells to produce pMCDN/mFcR4. The pMCDN vector, into which the neomycin resistance gene and the DHFR gene are inserted, enables induced expression under the control of the mouse CMV promoter (Accession No. U68299). The nucleotide sequence cloned was determined by sequencing using an ABI3730 DNA sequencer. The nucleotide sequence and the amino acid sequence of mouse FcγR4 are shown in SEQ ID NOs: 3 and 4, respectively. Compared to the known sequence (NM_144559), the nucleotide at position 422 had been changed from C to T in the sequence obtained; therefore, the amino acid at position 141 had been changed from serine to leucine.

1-2) Construction of Mouse FcγR3 Expression Vector

Using mouse spleen cDNA (Clontech) as a template, the mouse FcγR3 gene was amplified by PCR utilizing a sense primer containing an EcoRI restriction enzyme sequence (mFcR3-EcoRI-F, SEQ ID NO: 19) and an antisense primer containing a NotI restriction enzyme sequence (mFcR3-NotI-R, SEQ ID NO: 20). After treatment with the EcoRI and NotI restriction enzymes, the amplified product was cloned into the EcoRI-NotI site of the pMCDN plasmid to produce pMCDN/mFcR3. The nucleotide sequence cloned was determined by sequencing using an ABI3730 DNA sequencer. The nucleotide sequence and the amino acid sequence of mouse FcγR3 are shown in SEQ ID NOs: 1 and 2, respectively.

1-3) Construction of Mouse FcγR4/Human FcγR3 Chimeric Expression Vector

Using the pMCDN/mFcR4 plasmid, into which the mouse FcγR4 gene has been inserted, as a template, the extracellular domain of mouse FcγR4 was amplified by PCR utilizing a sense primer (mFcR4-EcoRI-F) and an antisense primer (m4h3-mR, SEQ ID NO: 21). Then, using the pMCDN/hFcR3 plasmid, which was prepared by inserting the human FcγR3 gene (nucleotide sequence: SEQ ID NO: 5; amino acid sequence: SEQ ID NO: 6) into pMCDN, as a template, the transmembrane domain and intracellular domain of human FcγR3 were amplified by PCR utilizing a sense primer (m4h3-hF, SEQ ID NO: 22) and an antisense primer (vector primer: pMCM-R1, SEQ ID NO: 23). After mixing these amplification products in an equal amount, the products were further amplified using the mFcR4-EcoRI-F primer and pMCM-R1 primer, treated with the EcoRI and NotI restriction enzymes, and then inserted into the EcoRI-NotI site of the pMCDN plasmid to construct the mouse FcγR4/human FcγR3 chimeric (mouse FcγR4/human FcγR3) expression vector (pMCDN/mFcR4-hFcR3). The nucleotide sequence cloned was determined by sequencing using an ABI3730 DNA sequencer. The nucleotide sequence and the amino acid sequence of mouse FcγR4/human FcγR3 are shown in SEQ ID NOs: 13 and 14, respectively.

1-4) Construction of Mouse FcγR4/Human γ Chain Chimeric Expression Vector

Using the pMCDN/mFcR4 plasmid, into which the mouse FcγR4 gene has been inserted, as a template, the extracellular domain of mouse FcγR4 was amplified by PCR utilizing a sense primer (mFcR4-EcoRI-F) and an antisense primer (m4hG-mR, SEQ ID NO: 24). Then, using human spleen cDNA (Clontech) as a template, the two amino acids of the extracellular domain, the transmembrane domain, and the intracellular domain of human γ chain (nucleotide sequence: SEQ ID NO: 7; amino acid sequence: SEQ ID NO: 8) were amplified by PCR utilizing a sense primer (m4hG-hF, SEQ ID NO: 25) and an antisense primer (m4hG-hR, SEQ ID NO: 26). After mixing these amplification products in an equal amount, the products were further amplified using the mFcR4-EcoRI-F primer and m4hG-hR primer, treated with the EcoRI restriction enzyme, and then inserted into the EcoRI-EcoRV site of the pMCDN plasmid to construct the mouse FcγR4/human γ chain chimeric (mouse FcγR4/human γ) expression vector (pMCDN/mFcR4-hG). The nucleotide sequence cloned was determined by sequencing using an ABI3730 DNA sequencer. The nucleotide sequence and the amino acid sequence of mouse FcγR4/human γ are shown in SEQ ID NOs: 15 and 16, respectively.

1-5) Construction of Mouse FcγR3/Human FcγR3 Chimeric Expression Vector

Using the pMCDN/mFcR3 plasmid, into which the mouse FcγR3 gene has been inserted, as a template, the extracellular domain of mouse FcγR3 was amplified by PCR utilizing a sense primer (mFcR3-EcoRI-F) and an antisense primer (m3h3-mR, SEQ ID NO: 27). Then, using the pMCDN/mFcR4-hFcR3 plasmid, into which the mouse FcγR4/human FcγR3 gene has been inserted, as a template, the transmembrane domain and intracellular domain of human FcγR3 was amplified by PCR utilizing a sense primer (m3h3-hF, SEQ ID NO: 28) and an antisense primer (pMCM-R1). After mixing these amplification products in an equal amount, the products were further amplified using the mFcR3-EcoRI-F primer and pMCM-R1 primer, treated with EcoRI and NotI restriction enzymes, and then inserted into the EcoRI-NotI site of the pMCDN plasmid to construct the mouse FcγR3/human FcγR3 chimeric (mouse FcγR3/human FcγR3) expression vector (pMCDN/mFcR3-hFcR3). The nucleotide sequence cloned was determined by sequencing using an ABI3730 DNA sequencer. The nucleotide sequence and the amino acid sequence of mouse FcγR3/human FcγR3 are shown in SEQ ID NOs: 9 and 10, respectively.

1-6) Construction of Mouse FcγR3/Human γ Chain Chimeric Expression Vector

Using the pMCDN/mFcR3 plasmid, into which the mouse FcγR3 gene has been inserted, as a template, the extracellular domain of mouse FcγR3 was amplified by PCR utilizing a sense primer (mFcR3-EcoRI-F) and an antisense primer (m3hG-mR, SEQ ID NO: 29). Then, using the pMCDN/mFcR4-hG plasmid, into which the mouse FcγR4/human γ gene has been inserted, as a template, the two amino acids of the extracellular domain, the transmembrane domain, and the intracellular domain of human γ chain were amplified by PCR utilizing a sense primer (m3hG-hF, SEQ ID NO: 30) and an antisense primer (pMCM-R1). After mixing these amplification products in an equal amount, the products were further amplified using the mFcR3-EcoRI-F primer and pMCM-R1 primer, treated with the EcoRI and NotI restriction enzymes, and then inserted into the EcoRI-NotI site of the pMCDN plasmid to construct the mouse FcγR3/human γ chain chimeric (mouse FcγR3/human γ) expression vector (pMCDN/mFcR3-hG). The nucleotide sequence and the amino acid sequence of mouse FcγR3/human γ are shown in SEQ ID NOs: 11 and 12, respectively.

1-7) Introduction of FcγR Expression Vector into NK92 Cell Line

NK92 cell lines that stably express mouse FcγR4/human FcγR3, mouse FcγR4/human γ, mouse FcγR3/human FcγR3, mouse FcγR3/human γ, and human FcγR3 were established by digesting the pMCDN/mFcR4-hFcR3, pMCDN/mFcR4-hG, pMCDN/mFcR3-hFcR3, pMCDN/mFcR3-hG, and pMCDN/hFcR3 plasmids with the PvuI restriction enzyme, then introducing the digested plasmids into the NK92 cell line (purchased from ATCC) by electroporation, and selecting the cells with 500 μg/mL Geneticin (Invitrogen). These NK92 cell lines were incubated in Alpha Minimum Essential Medium without ribonucleosides and deoxyribonucleosides with L-glutamine (Invitrogen) containing 500 μg/ml Geneticin, penicillin/streptomycin (Invitrogen), 100 U/ml recombinant human interleukin-2 (Peprotech), 10% fetal bovine serum (FBS, Invitrogen), 10% horse serum (Invitrogen), 0.11 mM 2-mercaptoethanol (Invitrogen), 0.2 mM inositol (Sigma), and 0.02 mM folic acid (Sigma).

Example 2

Preparation of Anti-Human Desmoglein 3 Antibody 2-1) Establishment of a Human Desmoglein 3 Expression Cell Line A CHO cell line stably expressing human desmoglein 3 (DSG3) (DSG3-DG44) was established by digesting the pMCN/DSG3 plasmid for expression in mammalian cells, into which the DSG3 gene (nucleotide sequence: SEQ ID NO: 31; amino acid sequence: SEQ ID NO: 32) has been inserted, with the Pvu I restriction enzyme, then introducing the digested plasmid into the CHO DG44 cell line (Invitrogen) by electroporation, and selecting the cells with 500 μg/mL Geneticin. pMCN enables induced expression under the control of the mouse CMV promoter (Accession No. U68299), and is a vector into which the neomycin resistance gene has been inserted. DSG3-DG44 cells were incubated in CHO-S-SFM II medium (Invitrogen) containing 500 μg/mL Geneticin, HT supplement (Invitrogen), and penicillin/streptomycin.

2-2) Preparation of Soluble Human Desmoglein 3/Mouse IgG2a-Fc Fusion Protein

Soluble human desmoglein 3/mouse IgG2a-Fc fusion protein (DSG3-Fc) was prepared as an immunizing antigen for producing anti-DSG3 antibodies. A gene constructed by linking the DSG3 extracellular domain (Met1-Leu616) with the mouse IgG2a constant region at the CpoI restriction enzyme sequence of the hinge region of the mouse IgG2a constant region (DSG3-Fc; nucleotide sequence: SEQ ID NO: 33; amino acid sequence: SEQ ID NO: 34) was cloned into the pMCDN plasmid to produce pMCDN/DSG3-Fc. A CHO cell line stably expressing DSG3-Fc (DSG3-Fc-DG44) was established by introducing the pMCDN/DSG3-Fc plasmid into DG44 cells by electroporation, and selecting the cells with 500 μg/mL of Geneticin. Then, DSG3-Fc was purified from the culture supernatant of DSG3-Fc-DG44. The culture supernatant was applied to a Hi Trap Protein G HP column (Cat. No. 17-0404-01, GE Healthcare Bio-Sciences), and after washing with a binding buffer (20 mM sodium phosphate, pH 7.0), elution was carried out using an elution buffer (0.1 M glycine-HCl, pH 2.7). The eluate was immediately neutralized by elution into a tube containing a neutralization buffer (1 M Tris-HCl (pH 9.0)). This eluate was subjected to gel filtration using Superdex 200 HR 10/30 (GE Healthcare Bio-Sciences) to replace the solvent with PBS. Purified DSG3-Fc was quantified using a DC protein assay kit (BIO-RAD) and converting to a concentration using bovine IgG included in the kit as standard.

2-3) Preparation of Anti-DSG3 Antibody

MRL/MpJUmmCrj-lpr/lpr mice (7- to 8-weeks old, purchased from Charles River Japan) were used as the animals for immunization. For the first immunization, 100 μg of DSG3-Fc was emulsified using Freund's complete adjuvant (Beckton Dickinson), and administered subcutaneously. Two weeks later, boosting immunization was carried out by emulsifying 50 μg of DSG3-Fc using Freund's incomplete adjuvant (Beckton Dickinson), and administering it subcutaneously. Thereafter, boosting immunizations were performed at one-week intervals for three times. For the final immunization, 50 μg of DSG3-Fc was administered into the tail vein. Four days after the final immunization, spleen cells were extirpated and mixed with mouse myeloma cells P3-X63Ag8U1 (purchased from ATCC) at 2:1 ratio, and cell fusion was carried out by addition of PEG 1500 (Roche Diagnostics). Then, RPMI 1640 medium (Invitrogen) was added, and then PEG 1500 was removed by centrifuging and removing the supernatant. The fused cells suspended in RPMI 1640 containing 10% FBS was seeded into a 96-well plate at 100 μL/well. On the following day, RPMI 1640 medium containing 10% FBS, 1×HAT media supplement (Sigma), and 0.5×BM-Condimed H1 Hybridoma cloning supplement (Roche Diagnostics) (HAT medium) was added at 100 μL/well. Two days later and three days later, half of the culture solution was replaced with HAT medium, and the day-7 culture supernatant was used for screening. The screening was performed by flow cytometry that detects binding to DSG3-DG44 cells. Positive clones obtained by this screening were monocloned by the limiting dilution method to establish a hybridoma that produces DF366, which is a monoclonal antibody that specifically binds to DSG3. This hybridoma was cultured in a HAT medium supplemented with Ultra-Low IgG FBS (Invitrogen) instead of FBS, and the DF366 antibody was purified from this culture supernatant using a Hi Trap Protein G HP column. The solvent was replaced with PBS using a PD-10 column (GE Healthcare Bio-Sciences). The concentration of the purified DF366 antibody was quantified using a DC protein assay kit. The isotype of the DF366 antibody was determined to be mouse IgG1κ by analysis using Isostrip (Roche Diagnostics).

Binding of the DF366 antibody to DSG3-DG44 cells was detected by flow cytometry. $5 \times 10^4$ cells of DSG3-DG44 was reacted with 3 µg/mL of DF366 antibody on ice for 30 minutes, and then washed. Then, this was reacted with an FITC-labeled anti-mouse IgG antibody (Beckman Coulter) as the secondary antibody on ice for 30 minutes, washed, and then subjected to flow cytometry. FACS Calibur (Becton Dickinson) was used as the flow cytometer. The DF366 antibody bound to DSG3-DG44 cells, but not to the parental DG44 cells. Therefore, the DF366 antibody was confirmed to bind specifically to DSG3.

2-4) Preparation of Human IgG1 Chimeric DF366 Antibody (DF366c)

The H-chain variable region gene (nucleotide sequence: SEQ ID NO: 35; amino acid sequence: SEQ ID NO: 36) and the L-chain variable region gene (nucleotide sequence: SEQ ID NO: 37; amino acid sequence: SEQ ID NO: 38) of DF366 antibody were cloned from a hybridoma that produces the DF366 antibody. Then, these genes were ligated in frame with the nucleotide sequences of the H-chain constant region gene and L-chain (κ-chain) constant region gene of human IgG1. PCR was performed using a primer having the 5'-end nucleotide sequence of the H-chain variable region gene, a Kozak sequence, and an EcoRI restriction enzyme sequence, and an antisense primer having a sequence complementary to the 3'-end nucleotide sequence and a NheI restriction enzyme sequence. PCR was also performed using a primer having the 5'-end nucleotide sequence of the L-chain variable region gene, a Kozak sequence, and a BamHI restriction enzyme sequence, and an antisense primer having a sequence complementary to the 3'-end nucleotide sequence and the BsiWI restriction enzyme sequence. The amplification products obtained were treated with the EcoRI and NheI restriction enzymes, or BamHI and BsiWI restriction enzymes, and inserted into the EcoRI-NheI site or BamHI-BsiWI site of the human IgG1 chimeric antibody expression plasmid (pMCDN/Glk), to produce pMCDN/Glk-DF366. pMCDN/Glk was produced by cloning the H-chain constant region gene (nucleotide sequence: SEQ ID NO: 39; amino acid sequence: SEQ ID NO: 40) and the L-chain (κ-chain) constant region gene (nucleotide sequence: SEQ ID NO: 41; amino acid sequence: SEQ ID NO: 42) of human IgG1 cloned, into the pMCDN plasmid. The mouse H-chain variable region and the human H-chain constant region were linked by a NheI restriction enzyme sequence, and the mouse L-chain variable region and the human L-chain constant region were linked by the BsiWI restriction enzyme sequence.

The pMCDN/Glk-DF366 plasmid was introduced into DG44 cells by electroporation. The CHO DF366c-DG44 cells, which stably express the human IgG1 chimeric DF366 antibody (DF366c), were established by selection with 500 µg/mL of Geneticin. The DF366c antibody was purified from the culture supernatant of DF366c-DG44 using a Hi Trap rProtein A column (GE Healthcare Bio-Science). The solvent was replaced with PBS using a PD-10 column. The concentration of the DF366c antibody purified was quantified using a DC protein assay kit. The nucleotide sequence of the full-length DF366c antibody H-chain gene and the corresponding amino acid sequence are shown in SEQ ID NOs: 43 and 44, respectively. The nucleotide sequence of the full length DF366c antibody L-chain gene and the corresponding amino acid sequence are shown in SEQ ID NOs: 45 and 46, respectively.

Binding of the DF366c antibody to DSG3-DG44 cells and DG44 cells was detected by flow cytometry. $3 \times 10^4$ cells were reacted with 10 µg/mL of DF366c antibody on ice for one hour, and then washed. Then, this was reacted with an FITC-labeled anti-human IgG antibody (Beckman Coulter) as the secondary antibody on ice for one hour, washed, and then subjected to flow cytometry. FACS Calibur (Becton Dickinson) was used as the flow cytometer. DF366c antibody bound to DSG3-DG44 cells, but not to the parental DG44 cells. Therefore, the DF366c antibody was confirmed to bind specifically to DSG3.

2-5) Preparation of Mouse IgG2a Chimeric DF366 Antibody (DF366m)

The nucleotide sequence of the DF366 antibody H-chain variable region gene was ligated in frame with the nucleotide sequence of the mouse IgG2a H-chain constant region gene. PCR was performed using a primer having the 5'-end nucleotide sequence of the H-chain variable region gene, a Kozak sequence, and an EcoRI restriction enzyme sequence, and an antisense primer having a cytosine residue attached to a sequence complementary to the 3'-end nucleotide sequence. The amplification product obtained was treated with the EcoRI restriction enzyme, and inserted into the EcoRI-NruI site of the mouse IgG2a chimeric H-chain expression plasmid (pMCD/G2a) to construct the mouse IgG2a chimeric DF366 antibody H chain expression vector (pMCD/G2a-DF366). pMCD/G2a was produced by cloning the mouse IgG2a H-chain constant region gene (nucleotide sequence: SEQ ID NO: 47; amino acid sequence: SEQ ID NO: 48) into the pMCD plasmid for expression in mammalian cells. The H-chain constant region was ligated to the H-chain variable region via the NruI restriction enzyme sequence. The pMCD vector, into which the DHFR gene is inserted, enables induced expression under the control of the mouse CMV promoter (Accession No. U68299).

The nucleotide sequence of the DF366 antibody L-chain variable region gene was ligated in frame with the nucleotide sequence of the L-chain (κ-chain) constant region gene of mouse IgG2a. PCR was performed using a primer having the 5'-end nucleotide sequence of the L-chain variable region gene, a Kozak sequence, and an EcoRI restriction enzyme sequence, and an antisense primer having "gcccg" residues attached to a sequence complementary to the 3'-end nucleotide sequence. The amplification product obtained was treated with the EcoRI restriction enzyme, and inserted into the EcoRI-NruI site of the mouse IgG2a chimeric L-chain (κ-chain) expression plasmid (pMCN/k) to construct the mouse IgG2a chimeric DF366 antibody L chain expression vector (pMCN/k-DF366). pMCN/k was produced by cloning the mouse IgG2a L-chain (κ-chain) constant region gene (nucleotide sequence: SEQ ID NO: 49; amino acid sequence: SEQ ID NO: 50) into the pMCN plasmid. The L-chain (κ-chain) constant region was ligated to the L-chain variable region via the NruT restriction enzyme sequence.

The pMCD/G2a-DF366 and pMCN/k-DF366 plasmids were introduced into DG44 cells by electroporation. The CHO DF366m-DG44 cells, which stably express the mouse IgG2a chimeric DF366 antibody (DF366m) were established by selection in a nucleic acid (HT supplement)-free medium containing 500 µg/mL of Geneticin. Subsequently, the DF366m antibody was purified from the culture supernatant of DF366m-DG44 using a Hi Trap Protein G HP column. The solvent was substituted with PBS using a PD-10 column. The concentration of the DF366m antibody purified was quantified using a DC Protein Assay kit. The DF366m antibody was subjected to flow cytometric analysis to confirm that the antibody specifically binds to DSG3 in the same way as the DF366c antibody. An FITC-labeled anti-mouse IgG antibody (Beckman Coulter) was used as the secondary antibody. The nucleotide sequence of the full-length DF366m antibody H-chain gene and the corresponding amino acid sequence are shown in SEQ ID NO: 51 and SEQ ID NO: 52, respectively. The nucleotide sequence of the full-length DF366m antibody L-chain gene and the corresponding amino acid sequence are shown in SEQ ID NO: 53 and SEQ ID NO: 54, respectively.

2-6) Production of Low-Fucose DF366 Antibody

The pMCDN/Glk-DF366 plasmid was introduced into a fucose transporter knockout CHO cell line (FTPKO-DXB11 cells, International Patent Publication Nos. WO 2006/067913 and WO 2006/067847) by electroporation. Low-fucose DF366c-DXB11, CHO cells stably expressing the low-fucose human IgG1 chimeric DF366 antibody (low-fucose DF366c), was established by selection with 500 µg/mL Geneticin. Subsequently, the low-fucose DF366c antibody was purified from the culture supernatant of low-fucose DF366c-DXB11 using a Hi Trap rProtein A column. The solvent was substituted with PBS using a PD-10 column, and the antibody concentration was quantified using a DC Protein Assay kit.

The pMCD/G2a-DF366 and pMCN/k-DF366 plasmids were introduced into FTPKO-DXB11 cells by electroporation. Low-fucose DF366m-DXB11, CHO cells stably expressing the low-fucose mouse IgG2a chimeric DF366 antibody (low-fucose DF366m), was established by selection in a nucleic acid (HT supplement)-free medium containing 500 µg/mL of Geneticin. Subsequently, the low-fucose DF366m antibody was purified from the culture supernatant of low-fucose DF366m-DXB11 using a Hi Trap Protein G HP column. The solvent was substituted with PBS using a PD-10 column, and the antibody concentration was quantified using a DC Protein Assay kit.

Example 3

Measurement of the ADCC Activity of Anti-DSG3 Antibody 3-1) Establishment of the Target Cell Line DSG3-Ba/F3, a Ba/F3 cell line stably expressing DSG3, was established by digesting, with the PvuI restriction enzyme, the pMCDN/DSG3 plasmid for expression in mammalian cells, into which the human desmoglein 3 (DSG3) gene (nucleotide sequence: SEQ ID NO: 31; amino acid sequence: SEQ ID NO: 32) has been inserted, then introducing the digested plasmid into Ba/F3 cells (purchased from RIKEN BioResource Center) by electroporation, and selecting the cells with 500 Geneticin. DSG3-Ba/F3 cells were incubated using RPMI 1640 medium (Invitrogen) containing 500 µg/mL Geneticin, penicillin/streptomycin, recombinant mouse interleukin-3 (R&D Systems), and 10% FBS.

Expression of DSG3 was determined by flow cytometry (FIG. 1). Specifically, DSG3-Ba/F3 cells were reacted with 10 µg/mL of an anti-DSG3 monoclonal antibody (R&D Systems) or a negative control antibody (mouse IgG2a, Becton Dickinson) on ice for one hour, and then washed. Subsequently, this was reacted with a secondary antibody (FITC-labeled anti-mouse Ig antibody, Becton Dickinson) on ice for one hour, washed, and then analyzed using a flow cytometer (FACS Calibur, Becton Dickinson).

3-2) Methods for Measuring the ADCC Activity

RPMI 1640 medium containing penicillin/streptomycin and 10% FBS (RPMI medium) was used for the experiment. $1\times10^6$ cells of the DSG3-Ba/F3 cell line were suspended in approximately 200 µL of RPMI medium containing 3.7 MBq of Chromium-51 (GE Healthcare Bio-Sciences), and then incubated in a 5% carbon dioxide gas incubator at 37° C. for one hour. After washing, the cell density was adjusted to $2\times10^5$ cells/mL, and then the cells were added to a 96-well U-bottomed plate at 50 µL/well. Then, 50 µL of an antibody solution was added to each well. The plate was left to stand at room temperature for 15 minutes, and then 100 µL of effector cells (described below) were added to each well. The plate was then left to stand in a 5% carbon dioxide gas incubator at 37° C. for four to six hours. Thereafter, 100 µL of the supernatant was collected from each well, and used for the radioactivity measurement on a gamma counter (1480 WIZARD 3", Wallac). The specific chromium release rate was calculated according to the following equation:

$$\text{Specific chromium release rate }(\%)=(A-C)\times100/(B-C)$$

where A represents the radioactivity (cpm) in each well, B represents the mean value of the radioactivity (cpm) in wells to which 50 µL of the cells and 150 µL of 2% Nonidet P-40 solution (Code No. 252-23, Nacalai Tesque) were added, and C represents the mean value of the radioactivity (cpm) in wells to which 50 µL of the cells and 150 µL of RPMI medium were added. The assay was conducted in duplicates, and the mean value and standard deviation were calculated for the specific chromium release rate.

3-3) Measurement of the ADCC Activity Using Mouse Spleen Cells as Effector Cells Cells (SPL) prepared by adding 50 ng/mL of recombinant human interleukin-2 (Peprotech) to spleen cells prepared from C3H mice (Charles River Japan), or cells (SPL-LAK) prepared by culturing spleen cells in the presence of 50 ng/mL of recombinant human interleukin-2 for four days were used as the effector cells. The ADCC activity was measured according to 3-2). The number of effector cells per well was $5\times10^5$ cells (SPL) or $2\times10^5$ cells (SPL-LAK), and the ADCC induction time was six hours. Mouse IgG2a (Becton Dickinson) and human IgG1 (Serotec) were used as the negative control antibodies.

Figure 2:
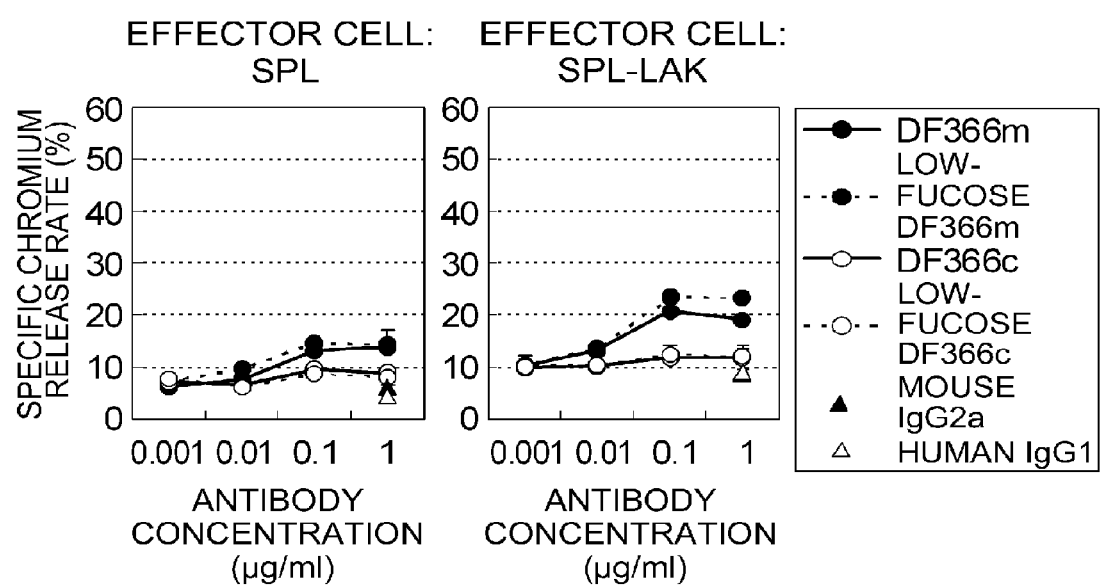
FIG. 2 shows the results of measuring the ADCC activity when mouse spleen cells were used as effector cells.

Low ADCC activity was detected for the DF366m antibody and low-fucose DF366m antibody, while hardly any ADCC activity was detected for the DF366c antibody and low-fucose DF366c antibody (FIG. 2).

3-4) Measurement of the ADCC Activity Using FcγR-Expressing NK92 Cell Lines as Effector Cells FcγR-expressing NK92 cell lines (Example 1, mouse FcγR4/human FcγR3-, mouse FcγR4/human γ-, mouse FcγR3/human FcγR3-, mouse FcγR3/human γ-, and human FcγR3-expressing NK92 cells) were used as the effector cells. The ADCC activity was measured according to 3-2).

The number of effector cells per well was 5×10⁴ cells, and the ADCC induction time was four hours. Mouse IgG2a (Becton Dickinson) and human IgG1 (Serotec) were used as the negative control antibodies.

Figure 3:
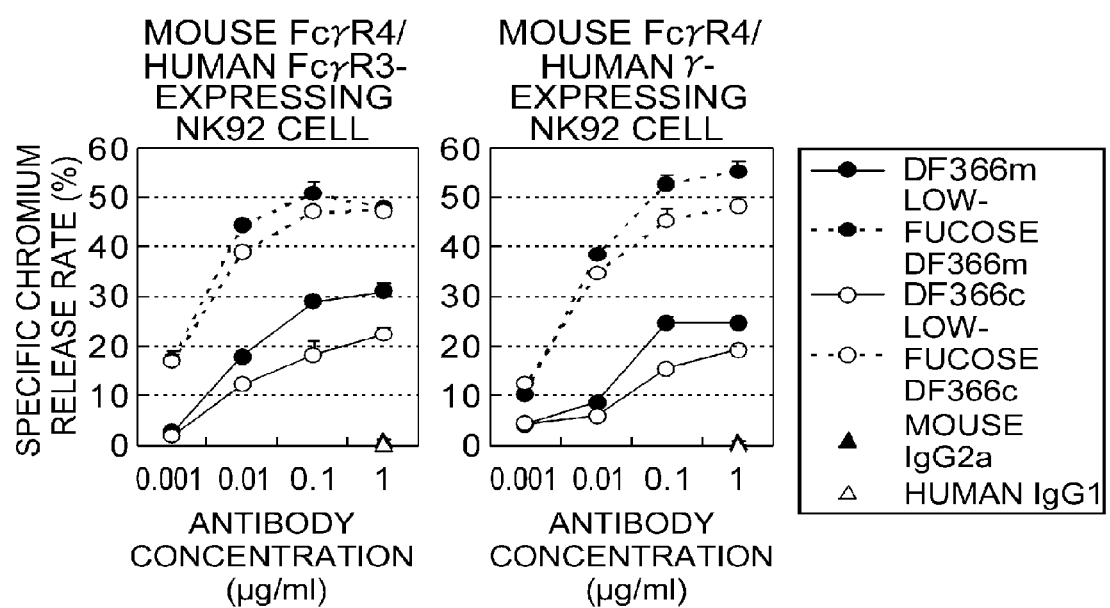
FIG. 3 shows the results of measuring the ADCC activity when mouse FcγR4/human FcγR3-expressing and mouse FcγR4/human γ-expressing NK92 cells were used as effector cells.

When mouse FcγR4/human FcγR3- and mouse FcγR4/human γ-expressing NK92 cells were used, the ADCC activity was detected for both the DF366m antibody and DF366c antibody, and the ADCC activity was more remarkably increased for the low-fucose DF366m antibody and low-fucose DF366c antibody (FIG. 3).

Figure 4:
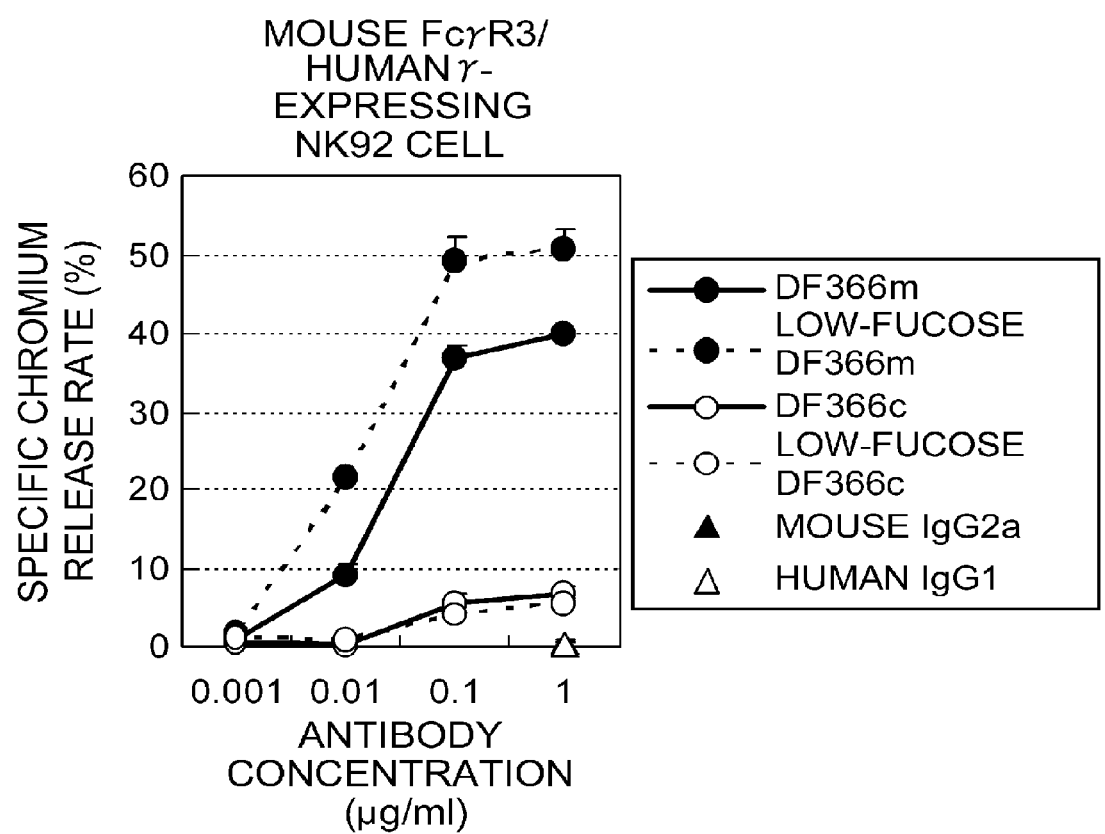
FIG. 4 shows the results of measuring the ADCC activity when mouse FcγR3/human γ-expressing NK92 cells were used as effector cells.

When mouse FcγR3/human γ-expressing NK92 cells were used, high ADCC activity was detected for the DF366m antibody, and the ADCC activity was further increased for the low-fucose DF366m antibody. Low ADCC activity was detected for the DF366c antibody and low-fucose DF366c antibody (FIG. 4).

Figure 5:
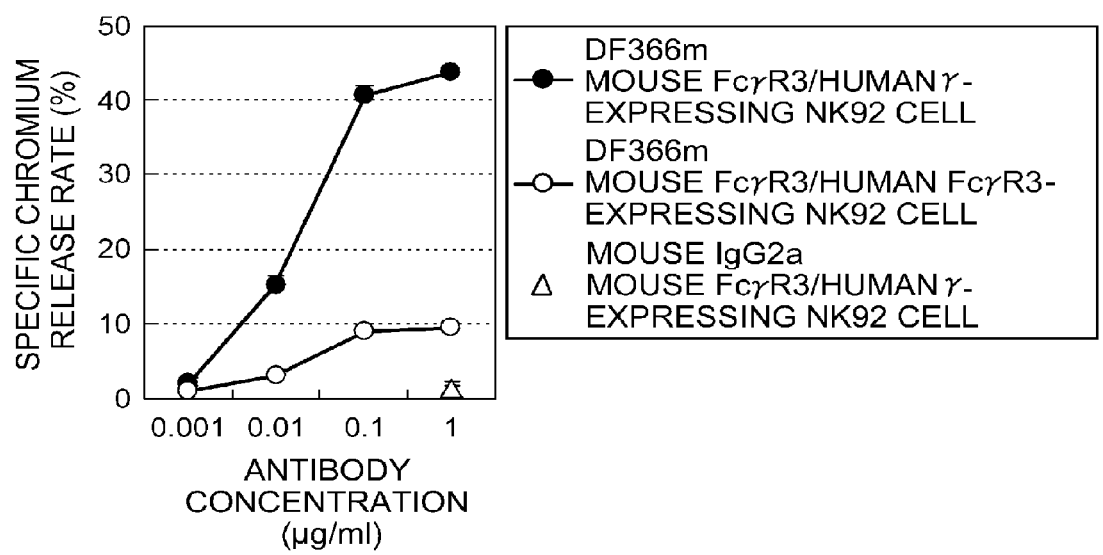
FIG. 5 shows the results of measuring the ADCC activity when mouse FcγR3/human FcγR3-expressing NK92 cells were used as effector cells.

The ADCC activity was low in mouse FcγR3/human FcγR3-expressing NK92 cells. This was speculated to be caused by low expression level of FcγR (FIG. 5).

Figure 6:
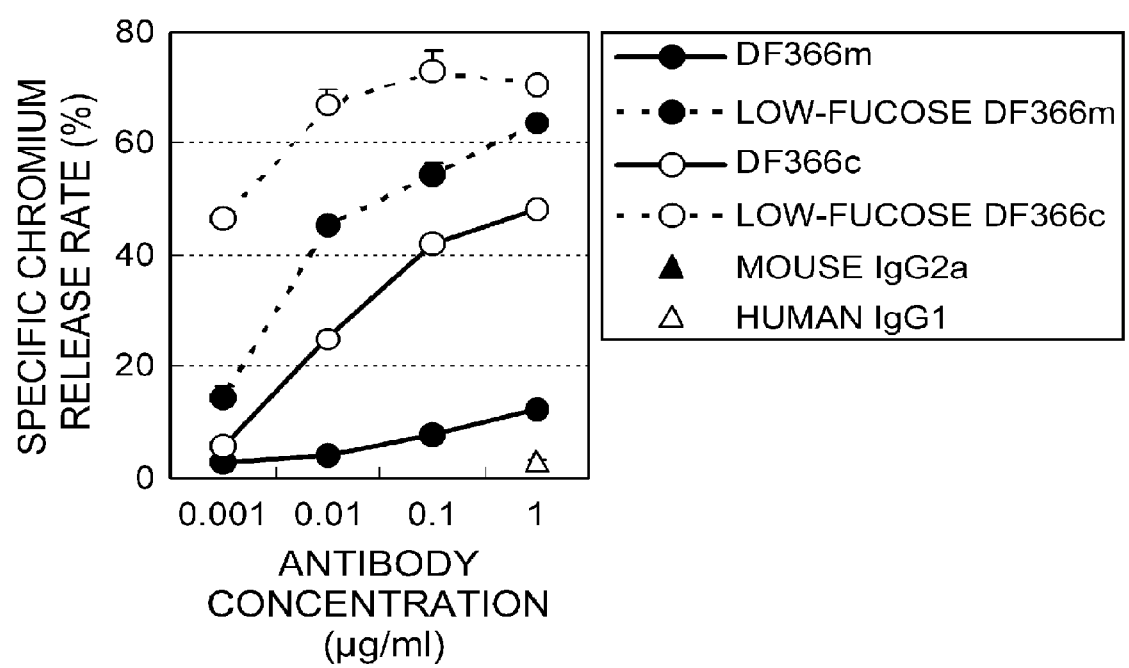
FIG. 6 shows the results of measuring the ADCC activity when human FcγR3-expressing NK92 cells were used as effector cells.

When using human FcγR3-expressing NK92 cells, high ADCC activity was detected for the DF366c antibody, and the ADCC activity was more remarkably increased for the low-fucose DF366c antibody. The DF366m antibody showed low ADCC activity, whereas high ADCC activity was detected for the low-fucose DF366m antibody (FIG. 6).

The above-mentioned results show that high ADCC activity can be detected when using chimeric FcγR-expressing NK92 cells, even if only low ADCC activity can be detected in mouse spleen cells. In particular, in mouse FcγR4-expressing NK92 cells, enhancement of the ADCC activity by the low-fucose antibodies was clearly demonstrated. In human FcγR3-expressing NK92 cells, the ADCC activity of the mouse antibodies could not be sufficiently detected. Thus, it was shown that chimeric FcγR-expressing NK92 cells are advantageous for measuring the ADCC activity of mouse antibodies.

Example 4

Measurement of the ADCC Activity of Anti-Claudin 3 Antibody

Figure 7:
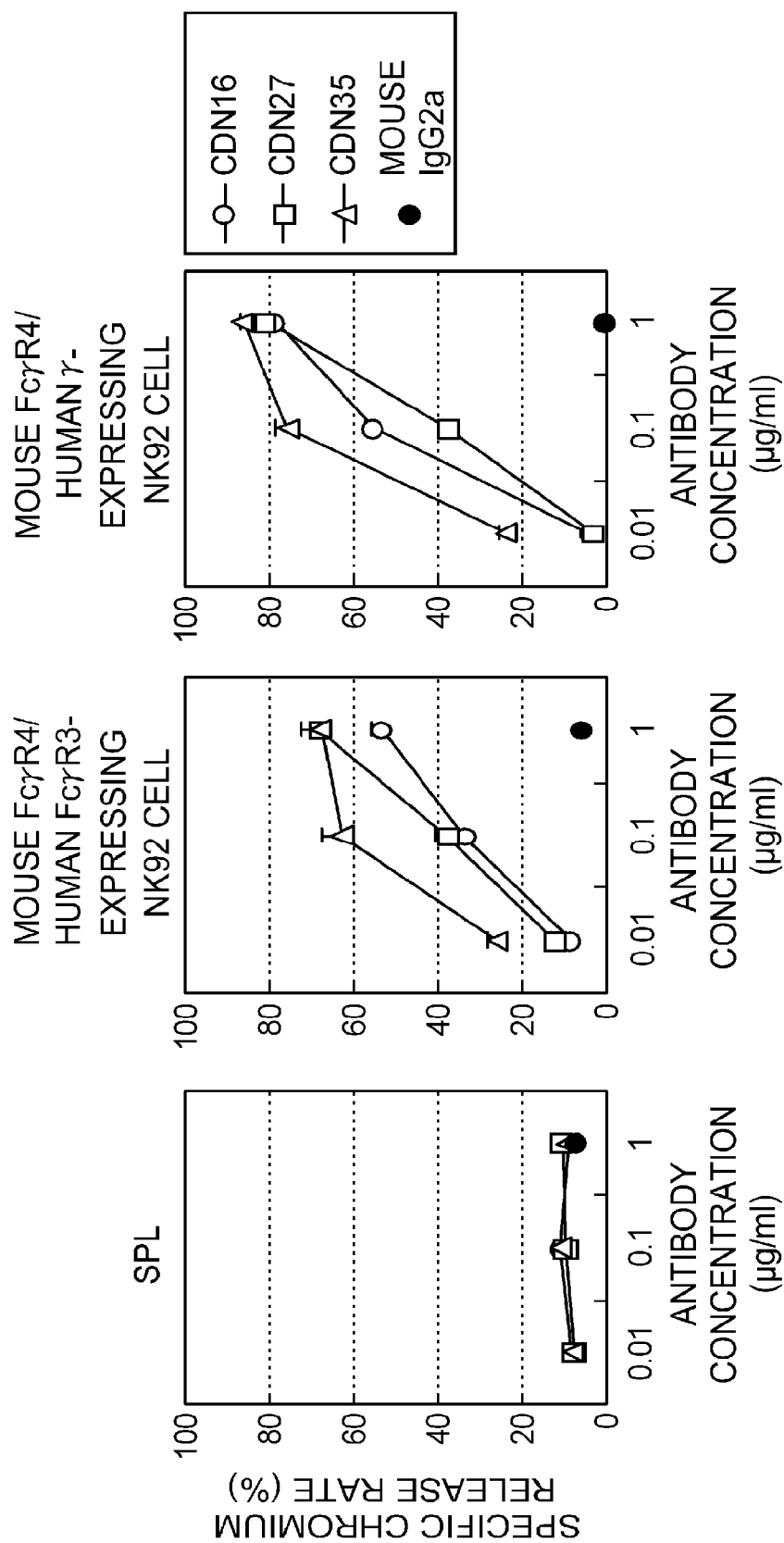
FIG. 7 shows the results of measuring the ADCC activity of anti-claudin3 monoclonal antibodies.

The ADCC activity of anti-claudin 3 monoclonal antibody was measured (FIG. 7). The MCF7 breast cancer cell line (purchased from ATCC) was used as target cells, and the measurements were performed as described in Example 3. The antibodies used were CDN16 (mouse IgG2b, H-chain amino acid sequence: SEQ ID NO: 55; L-chain amino acid sequence: SEQ ID NO: 56), CDN27 (mouse IgG2a, H-chain amino acid sequence: SEQ ID NO: 57, L-chain amino acid sequence: SEQ ID NO: 58), and CDN35 (mouse IgG2a, H-chain amino acid sequence: SEQ ID NO: 59, L-chain amino acid sequence: SEQ ID NO: 60). When SPL (4.5×10⁵ cells/well, and ADCC induction time of six hours) was used as the effector cells, hardly any ADCC activity could be detected. When mouse FcγR4/human FcγR3- and mouse FcγR4/human γ-expressing NK92 cells were used (5×10⁴ cells/well, and ADCC induction time of four hours), significant ADCC activity was detected. Among them, CDN35 showed high ADCC activity.

The above-mentioned results show that the use of chimeric FcγR-expressing NK92 cells enables detection of the ADCC activity, and allows accurate comparison of the ADCC activity of each antibody, even if the ADCC activity could not be detected sufficiently in mouse spleen cells.

INDUSTRIAL APPLICABILITY

Expression of chimeric proteins of the present invention in effector cells greatly reduces the labor for preparing effector cells for measuring the ADCC activity of mouse antibodies, and enables accurate measurements with small lot-to-lot differences. By utilizing effector cells expressing the chimeric proteins of the present invention, antibodies having cytotoxic activity, which are used for the treatment or prevention of diseases such as cancers or autoimmune diseases, can be efficiently screened.

The invention claimed is:

1. A method of screening for an antibody having cytotoxic activity, wherein the method comprises:
   (a) contacting a test antibody with a cell expressing an antigen to which the test antibody binds;
   (b) contacting the test antibody of (a) with a cell expressing a chimeric protein, wherein the chimeric protein comprises a mouse Fcγ receptor extracellular domain and a human γ chain transmembrane domain;
   (c) measuring the cytotoxic activity of the test antibody; and
   (d) selecting an antibody having cytotoxic activity.

2. The screening method of claim 1, wherein the test antibody is a mouse antibody.

3. A method of screening for an antibody having cytotoxic activity, wherein the method comprises:
   (a) contacting a test antibody with a cell expressing an antigen to which the test antibody binds;
   (b) contacting the test antibody of (a) with a cell expressing a chimeric protein, wherein the chimeric protein comprises a mouse Fcγ receptor extracellular domain and a human Fcγ receptor transmembrane domain;
   (c) measuring the cytotoxic activity of the test antibody; and
   (d) selecting an antibody having cytotoxic activity.

4. The screening method of claim 3, wherein the test antibody is a mouse antibody.

5. The screening method of claim 1, wherein the cell is an NK cell.

6. The screening method of claim 1, wherein the chimeric protein further comprises a human γ chain intracellular domain.

7. The screening method of claim 1, wherein the mouse Fcγ receptor is mouse Fcγ receptor 3.

8. The screening method of claim 1, wherein the mouse Fcγ receptor is mouse Fcγ receptor 4.

9. The screening method of claim 3, wherein the cell is an NK cell.

10. The screening method of claim 3, wherein the chimeric protein further comprises a human Fcγ receptor intracellular domain.

11. The screening method of claim 3, wherein the human Fcγ receptor is human Fcγ receptor 3.

12. The screening method of claim 3, wherein the mouse Fcγ receptor is mouse Fcγ receptor 3.

13. The screening method of claim 3, wherein the mouse Fcγ receptor is mouse Fcγ receptor 4.

14. The screening method of claim 1, wherein the mouse Fcγ receptor extracellular domain has the amino acid sequence of the extracellular domain of SEQ ID NO: 2.

15. The screening method of claim 1, wherein the mouse Fcγ receptor extracellular domain has the amino acid sequence of the extracellular domain of SEQ ID NO: 4.

16. The screening method of claim 1, wherein the human γ chain transmembrane domain has the amino acid sequence of the transmembrane domain of SEQ ID NO: 8.

17. The screening method of claim 3, wherein the mouse Fcγ receptor extracellular domain has the amino acid sequence of the extracellular domain of SEQ ID NO: 2.

18. The screening method of claim 3, wherein the mouse Fcγ receptor extracellular domain has the amino acid sequence of the extracellular domain of SEQ ID NO: 4.

19. The screening method of claim 3, wherein the human Fcγ receptor transmembrane domain has the amino acid sequence of the transmembrane domain of SEQ ID NO: 6.

* * * * *

SEQUENCE LISTING

```
<160> NUMBER OF SEQ ID NOS: 60

<210> SEQ ID NO 1
<211> LENGTH: 786
<212> TYPE: DNA
<213> ORGANISM: Mus musculus

<400> SEQUENCE: 1
atgtttcaga  atgcacactc  tggaagccaa  tggctacttc  caccactgac  aattctgctg    60
ctgtttgctt  ttgcagacag  gcagagtgca  gctcttccga  aggctgtggt  gaaactggac   120
cccccatgga  tccaggtgct  caaggaagac  atggtgacga  tgatgtgcga  agggacccac   180
aaccctggga  actcttctac  ccagtggttc  cacaacggga  ggtccatccg  gagccaggtc   240
caagccagtt  acacgtttaa  ggccacagtc  aatgacagtg  gagaatatcg  gtgtcaaatg   300
gagcagaccc  gcctcagcga  ccctgtagat  ctgggagtga  tttctgactg  gctgctgctc   360
cagacccctc  agcgggtgtt  tctggaaggg  gaaaccatca  cgctaaggtg  ccatagctgg   420
aggaacaaac  tactgaacag  gatctcattc  ttccataatg  aaaaatccgt  gaggtatcat   480
cactacaaaa  gtaatttctc  tatcccaaaa  gccaaccaca  gtcacagtgg  ggactactac   540
tgcaaaggaa  gtctaggaag  tacacagcac  cagtccaagc  ctgtcaccat  cactgtccaa   600
gatccagcaa  ctacatcctc  catctctcta  gtctggtacc  acactgcttt  ctccctagtg   660
```

| | |
|---|---:|
| atgtgcctcc tgtttgcagt ggacacgggc ctttatttct acgtacggag aaatcttcaa | 720 |
| accccgaggg agtactggag gaagtccctg tcaatcagaa agcaccaggc tcctcaagac | 780 |
| aagtga | 786 |

```
<210> SEQ ID NO 2
<211> LENGTH: 261
<212> TYPE: PRT
<213> ORGANISM: Mus musculus

<400> SEQUENCE: 2

Met Phe Gln Asn Ala His Ser Gly Ser Gln Trp Leu Leu Pro Pro Leu
1               5                   10                  15

Thr Ile Leu Leu Leu Phe Ala Phe Ala Asp Arg Gln Ser Ala Ala Leu
            20                  25                  30

Pro Lys Ala Val Val Lys Leu Asp Pro Pro Trp Ile Gln Val Leu Lys
        35                  40                  45

Glu Asp Met Val Thr Leu Met Cys Glu Gly Thr His Asn Pro Gly Asn
    50                  55                  60

Ser Ser Thr Gln Trp Phe His Asn Gly Arg Ser Ile Arg Ser Gln Val
65                  70                  75                  80

Gln Ala Ser Tyr Thr Phe Lys Ala Thr Val Asn Asp Ser Gly Glu Tyr
                85                  90                  95

Arg Cys Gln Met Glu Gln Thr Arg Leu Ser Asp Pro Val Asp Leu Gly
            100                 105                 110

Val Ile Ser Asp Trp Leu Leu Leu Gln Thr Pro Gln Arg Val Phe Leu
        115                 120                 125

Glu Gly Glu Thr Ile Thr Leu Arg Cys His Ser Trp Arg Asn Lys Leu
    130                 135                 140

Leu Asn Arg Ile Ser Phe Phe His Asn Glu Lys Ser Val Arg Tyr His
145                 150                 155                 160

His Tyr Lys Ser Asn Phe Ser Ile Pro Lys Ala Asn His Ser His Ser
                165                 170                 175

Gly Asp Tyr Tyr Cys Lys Gly Ser Leu Gly Ser Thr Gln His Gln Ser
            180                 185                 190

Lys Pro Val Thr Ile Thr Val Gln Asp Pro Ala Thr Thr Ser Ser Ile
        195                 200                 205

Ser Leu Val Trp Tyr His Thr Ala Phe Ser Leu Val Met Cys Leu Leu
    210                 215                 220

Phe Ala Val Asp Thr Gly Leu Tyr Phe Tyr Val Arg Arg Asn Leu Gln
225                 230                 235                 240

Thr Pro Arg Glu Tyr Trp Arg Lys Ser Leu Ser Ile Arg Lys His Gln
                245                 250                 255

Ala Pro Gln Asp Lys
            260

<210> SEQ ID NO 3
<211> LENGTH: 750
<212> TYPE: DNA
<213> ORGANISM: Mus musculus

<400> SEQUENCE: 3
```

| | |
|---|---:|
| atgtggcagc tactactacc aacagctctg gtacttacag ctttctctgg cattcaagct | 60 |
| ggtctccaaa aggctgtggt gaacctagac cccaagtggg tcagggtgct tgaggaagac | 120 |
| agcgtgaccc tcagatgcca aggcacttc tcccccgagg acaattctat caagtggttc | 180 |

```
cataacgaaa gcctcatccc acaccaggat gccaactatg tcatccaaag tgccagagtt      240
aaggacagtg gaatgtacag gtgccagaca gccctctcca cgatcagtga cccagtgcaa      300
ctagaggtcc atatgggctg gctattgctt cagaccacta agtggctgtt ccaggagggg      360
gaccccattc atctgagatg ccacagttgg caaaacagac ctgtacggaa ggtcacctat      420
tcacagaacg gcaaggcaa gaagtatttc catgaaaatt ctgaattact cattccaaaa       480
gctacacaca atgacagtgg ctcctacttc tgcagagggc tcattggaca caacaacaaa      540
tcttcagcat cctttcgtat aagcctaggc gatccagggt ctccatccat gtttccaccg      600
tggcatcaaa tcacattctg cctgctgata ggactcttgt ttgcaataga cacagtgctg      660
tatttctctg tgcggagggg tcttcaaagt cctgtggctg actatgagga acccaagatt      720
caatggagca aggaacctca ggacaagtga                                        750
```

\<210\> SEQ ID NO 4
\<211\> LENGTH: 249
\<212\> TYPE: PRT
\<213\> ORGANISM: Mus musculus

\<400\> SEQUENCE: 4

```
Met Trp Gln Leu Leu Pro Thr Ala Leu Val Leu Thr Ala Phe Ser
1               5                   10                  15

Gly Ile Gln Ala Gly Leu Gln Lys Ala Val Val Asn Leu Asp Pro Lys
            20                  25                  30

Trp Val Arg Val Leu Glu Glu Asp Ser Val Thr Leu Arg Cys Gln Gly
        35                  40                  45

Thr Phe Ser Pro Glu Asp Asn Ser Ile Lys Trp Phe His Asn Glu Ser
    50                  55                  60

Leu Ile Pro His Gln Asp Ala Asn Tyr Val Ile Gln Ser Ala Arg Val
65                  70                  75                  80

Lys Asp Ser Gly Met Tyr Arg Cys Gln Thr Ala Leu Ser Thr Ile Ser
                85                  90                  95

Asp Pro Val Gln Leu Glu Val His Met Gly Trp Leu Leu Gln Thr
            100                 105                 110

Thr Lys Trp Leu Phe Gln Glu Gly Asp Pro Ile His Leu Arg Cys His
        115                 120                 125

Ser Trp Gln Asn Arg Pro Val Arg Lys Val Thr Tyr Ser Gln Asn Gly
    130                 135                 140

Lys Gly Lys Lys Tyr Phe His Glu Asn Ser Glu Leu Leu Ile Pro Lys
145                 150                 155                 160

Ala Thr His Asn Asp Ser Gly Ser Tyr Phe Cys Arg Gly Leu Ile Gly
                165                 170                 175

His Asn Asn Lys Ser Ser Ala Ser Phe Arg Ile Ser Leu Gly Asp Pro
            180                 185                 190

Gly Ser Pro Ser Met Phe Pro Pro Trp His Gln Ile Thr Phe Cys Leu
        195                 200                 205

Leu Ile Gly Leu Leu Phe Ala Ile Asp Thr Val Leu Tyr Phe Ser Val
    210                 215                 220

Arg Arg Gly Leu Gln Ser Pro Val Ala Asp Tyr Glu Glu Pro Lys Ile
225                 230                 235                 240

Gln Trp Ser Lys Glu Pro Gln Asp Lys
                245
```

\<210\> SEQ ID NO 5
\<211\> LENGTH: 765

```
<212> TYPE: DNA
<213> ORGANISM: Homo sapiens

<400> SEQUENCE: 5
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactcccctg aggacaattc cacacagtgg     180
tttcacaatg agagcctcat ctcaagccag gcctcgagct acttcattga cgctgccaca     240
gtcgacgaca gtggagagta caggtgccag acaaacctct ccaccctcag tgacccggtg     300
cagctagaag tccatatcgg ctggctgttg ctccaggccc ctcggtgggt gttcaaggag     360
gaagaccta ttcacctgag gtgtcacagc tggaagaaca ctgctctgca taaggtcaca     420
tatttacaga atggcaaagg caggaagtat tttcatcata attctgactt ctacattcca     480
aaagccacac tcaaagacag cggctcctac ttctgcaggg ggcttgttgg gagtaaaaat     540
gtgtcttcag agactgtgaa catcaccatc actcaaggtt tggcagtgtc aaccatctca     600
tcattctttc cacctgggta ccaagtctct ttctgcttgg tgatggtact ccttttttgca    660
gtggacacag gactatattt ctctgtgaag acaaacattc gaagctcaac aagagactgg     720
aaggaccata atttaaatg gagaaaggac cctcaagaca aatga                      765

<210> SEQ ID NO 6
<211> LENGTH: 254
<212> TYPE: PRT
<213> ORGANISM: Homo sapiens

<400> SEQUENCE: 6

Met Trp Gln Leu Leu Pro Thr Ala Leu Leu Leu Val Ser Ala
1               5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
```

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
            245                 250

<210> SEQ ID NO 7
<211> LENGTH: 261
<212> TYPE: DNA
<213> ORGANISM: Homo sapiens

<400> SEQUENCE: 7
atgattccag cagtggtctt gctcttactc cttttggttg aacaagcagc ggccctggga      60
gagcctcagc tctgctatat cctggatgcc atcctgtttc tgtatggaat tgtcctcacc     120
ctcctctact gtcgactgaa gatccaagtg cgaaaggcag ctataaccag ctatgagaaa     180
tcagatggtg tttacacggg cctgagcacc aggaaccagg agacttacga gactctgaag     240
catgagaaac caccacagta g                                               261

<210> SEQ ID NO 8
<211> LENGTH: 86
<212> TYPE: PRT
<213> ORGANISM: Homo sapiens

<400> SEQUENCE: 8

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
            85

<210> SEQ ID NO 9
<211> LENGTH: 783
<212> TYPE: DNA
<213> ORGANISM: Artificial
<220> FEATURE:
<223> OTHER INFORMATION: An artificially synthesized nucleotide sequence

<400> SEQUENCE: 9
atgtttcaga atgcacactc tggaagccaa tggctacttc caccactgac aattctgctg      60
ctgtttgctt ttgcagacag gcagagtgca gctcttccga aggctgtggt gaaactggac     120
cccccatgga tccaggtgct caaggaagac atggtgacat gatgtgcga agggacccac     180 aaccctggga actcttctac ccagtggttc acaacgggga ggtccatccg gagccaggtc     240
caagccagtt acacgtttaa ggccacagtc aatgacagtg agaatatcg gtgtcaaatg      300 gagcagaccc gcctcagcga ccctgtagat ctgggagtga tttctgactg gctgctgctc     360 cagaccctc agcgggtgtt tctggaaggg gaaaccatca cgctaaggtg ccatagctgg     420
aggaacaaac tactgaacag gatctcattc ttccataatg aaaaatccgt gaggtatcat     480
cactacaaaa gtaatttctc tatcccaaaa gccaaccaca gtcacagtgg ggactactac     540

```
tgcaaaggaa gtctaggaag tacacagcac cagtccaagc ctgtcaccat cactgtccaa     600
gatccagcaa ctcatcctc catctctcta gtctggtacc aagtctcttt ctgcttggtg      660
atggtactcc tttttgcagt ggacacagga ctatatttct ctgtgaagac aaacattcga    720
agctcaacaa gagactggaa ggaccataaa tttaaatgga gaaggaccc tcaagacaaa    780 tga                                                                   783
```

<210> SEQ ID NO 10
<211> LENGTH: 260
<212> TYPE: PRT
<213> ORGANISM: Artificial
<220> FEATURE:
<223> OTHER INFORMATION: An artificially synthesized peptide sequence

<400> SEQUENCE: 10

```
Met Phe Gln Asn Ala His Ser Gly Ser Gln Trp Leu Leu Pro Pro Leu
1               5                   10                  15

Thr Ile Leu Leu Leu Phe Ala Phe Ala Asp Arg Gln Ser Ala Ala Leu
            20                  25                  30

Pro Lys Ala Val Val Lys Leu Asp Pro Pro Trp Ile Gln Val Leu Lys
        35                  40                  45

Glu Asp Met Val Thr Leu Met Cys Glu Gly Thr His Asn Pro Gly Asn
50                  55                  60

Ser Ser Thr Gln Trp Phe His Asn Gly Arg Ser Ile Arg Ser Gln Val
65                  70                  75                  80

Gln Ala Ser Tyr Thr Phe Lys Ala Thr Val Asn Asp Ser Gly Glu Tyr
                85                  90                  95

Arg Cys Gln Met Glu Gln Thr Arg Leu Ser Asp Pro Val Asp Leu Gly
            100                 105                 110

Val Ile Ser Asp Trp Leu Leu Leu Gln Thr Pro Gln Arg Val Phe Leu
        115                 120                 125

Glu Gly Glu Thr Ile Thr Leu Arg Cys His Ser Trp Arg Asn Lys Leu
130                 135                 140

Leu Asn Arg Ile Ser Phe Phe His Asn Glu Lys Ser Val Arg Tyr His
145                 150                 155                 160

His Tyr Lys Ser Asn Phe Ser Ile Pro Lys Ala Asn His Ser His Ser
                165                 170                 175

Gly Asp Tyr Tyr Cys Lys Gly Ser Leu Gly Ser Thr Gln His Gln Ser
            180                 185                 190

Lys Pro Val Thr Ile Thr Val Gln Asp Pro Ala Thr Thr Ser Ser Ile
        195                 200                 205

Ser Leu Val Trp Tyr Gln Val Ser Phe Cys Leu Val Met Val Leu Leu
210                 215                 220

Phe Ala Val Asp Thr Gly Leu Tyr Phe Ser Val Lys Thr Asn Ile Arg
225                 230                 235                 240

Ser Ser Thr Arg Asp Trp Lys Asp His Lys Phe Lys Trp Arg Lys Asp
                245                 250                 255

Pro Gln Asp Lys
            260
```

<210> SEQ ID NO 11
<211> LENGTH: 834
<212> TYPE: DNA
<213> ORGANISM: Artificial
<220> FEATURE:
<223> OTHER INFORMATION: An artificially synthesized nucleotide sequence

<400> SEQUENCE: 11

```
atgtttcaga atgcacactc tggaagccaa tggctacttc caccactgac aattctgctg      60
ctgtttgctt ttgcagacag gcagagtgca gctcttccga aggctgtggt gaaactggac     120
cccccatgga tccaggtgct caaggaagac atggtgacac tgatgtgcga agggacccac     180
aaccctggga actcttctac ccagtggttc acaacgggga ggtccatccg gagccaggtc     240
caagccagtt acacgtttaa ggccacagtc aatgacagtg gagaatatcg cgtgtcaaatg    300
gagcagaccc gcctcagcga ccctgtagat ctgggagtga tttctgactg gctgctgctc     360
cagacccctc agcgggtgtt tctggaaggg gaaaccatca cgctaaggtg ccatagctgg     420
aggaacaaac tactgaacag gatctcattc ttccataatg aaaaatccgt gaggtatcat     480
cactacaaaa gtaatttctc tatcccaaaa gccaaccaca gtcacagtgg ggactactac     540
tgcaaaggaa gtctaggaag tacacagcac cagtccaagc ctgtcaccat cactgtccaa     600
gatccagcaa ctacatcctc catctctcta gtctggcctc agctctgcta tatcctggat     660
gccatcctgt ttctgtatgg aattgtcctc accctcctct actgtcgact gaagatccaa     720
gtgcgaaagg cagctataac cagctatgag aaatcagatg gtgtttacac gggcctgagc     780
accaggaacc aggagactta cgagactctg aagcatgaga aaccaccaca gtag            834
```

<210> SEQ ID NO 12
<211> LENGTH: 277
<212> TYPE: PRT
<213> ORGANISM: Artificial
<220> FEATURE:
<223> OTHER INFORMATION: An artificially synthesized peptide sequence

<400> SEQUENCE: 12

```
Met Phe Gln Asn Ala His Ser Gly Ser Gln Trp Leu Leu Pro Pro Leu
1               5                   10                  15

Thr Ile Leu Leu Leu Phe Ala Phe Ala Asp Arg Gln Ser Ala Ala Leu
            20                  25                  30

Pro Lys Ala Val Val Lys Leu Asp Pro Pro Trp Ile Gln Val Leu Lys
        35                  40                  45

Glu Asp Met Val Thr Leu Met Cys Glu Gly Thr His Asn Pro Gly Asn
    50                  55                  60

Ser Ser Thr Gln Trp Phe His Asn Gly Arg Ser Ile Arg Ser Gln Val
65                  70                  75                  80

Gln Ala Ser Tyr Thr Phe Lys Ala Thr Val Asn Asp Ser Gly Glu Tyr
                85                  90                  95

Arg Cys Gln Met Glu Gln Thr Arg Leu Ser Asp Pro Val Asp Leu Gly
            100                 105                 110

Val Ile Ser Asp Trp Leu Leu Leu Gln Thr Pro Gln Arg Val Phe Leu
        115                 120                 125

Glu Gly Glu Thr Ile Thr Leu Arg Cys His Ser Trp Arg Asn Lys Leu
    130                 135                 140

Leu Asn Arg Ile Ser Phe Phe His Asn Glu Lys Ser Val Arg Tyr His
145                 150                 155                 160

His Tyr Lys Ser Asn Phe Ser Ile Pro Lys Ala Asn His Ser His Ser
                165                 170                 175

Gly Asp Tyr Tyr Cys Lys Gly Ser Leu Gly Ser Thr Gln His Gln Ser
            180                 185                 190

Lys Pro Val Thr Ile Thr Val Gln Asp Pro Ala Thr Thr Ser Ser Ile
        195                 200                 205
```

Ser Leu Val Trp Pro Gln Leu Cys Tyr Ile Leu Asp Ala Ile Leu Phe
    210                 215                 220

Leu Tyr Gly Ile Val Leu Thr Leu Leu Tyr Cys Arg Leu Lys Ile Gln
225                 230                 235                 240

Val Arg Lys Ala Ala Ile Thr Ser Tyr Glu Lys Ser Asp Gly Val Tyr
                245                 250                 255

Thr Gly Leu Ser Thr Arg Asn Gln Glu Thr Tyr Glu Thr Leu Lys His
            260                 265                 270

Glu Lys Pro Pro Gln
        275

<210> SEQ ID NO 13
<211> LENGTH: 750
<212> TYPE: DNA
<213> ORGANISM: Artificial
<220> FEATURE:
<223> OTHER INFORMATION: An artificially synthesized nucleotide sequence

<400> SEQUENCE: 13
atgtggcagc tactactacc aacagctctg gtacttacag ctttctctgg cattcaagct      60
ggtctccaaa aggctgtggt gaacctagac cccaagtggg tcagggtgct tgaggaagac     120
agcgtgaccc tcagatgcca aggcactttc tcccccgagg acaattctat caagtggttc     180
cataacgaaa gcctcatccc acaccaggat gccaactatg tcatccaaag tgccagagtt     240
aaggacagtg gaatgtacag gtgccagaca gccctctcca cgatcagtga cccagtgcaa     300
ctagaggtcc atatgggctg gctattgctt cagaccacta gtggctgtt ccaggagggg     360 gaccccattc atctgagatg ccacagttgg caaaacagac ctgtacggaa ggtcacctat     420
tcacagaacg gcaaaggcaa gaagtatttc catgaaaatt ctgaattact cattccaaaa     480
gctacacaca atgacagtgg ctcctacttc tgcagagggc tcattggaca caacaacaaa     540
tcttcagcat cctttcgtat aagcctaggc gatccaggt ctccatccat gtttccaccg     600
tggtaccaag tctctttctg cttggtgatg gtactccttt ttgcagtgga cacaggacta     660
tatttctctg tgaagacaaa cattcgaagc tcaacaagag actggaagga ccataaattt     720
aaatggagaa aggaccctca agacaaatga                                      750

<210> SEQ ID NO 14
<211> LENGTH: 249
<212> TYPE: PRT
<213> ORGANISM: Artificial
<220> FEATURE:
<223> OTHER INFORMATION: An artificially synthesized peptide sequence

<400> SEQUENCE: 14

Met Trp Gln Leu Leu Leu Pro Thr Ala Leu Val Leu Thr Ala Phe Ser
1               5                   10                  15

Gly Ile Gln Ala Gly Leu Gln Lys Ala Val Val Asn Leu Asp Pro Lys
            20                  25                  30

Trp Val Arg Val Leu Glu Glu Asp Ser Val Thr Leu Arg Cys Gln Gly
        35                  40                  45

Thr Phe Ser Pro Glu Asp Asn Ser Ile Lys Trp Phe His Asn Glu Ser
    50                  55                  60

Leu Ile Pro His Gln Asp Ala Asn Tyr Val Ile Gln Ser Ala Arg Val
65                  70                  75                  80

Lys Asp Ser Gly Met Tyr Arg Cys Gln Thr Ala Leu Ser Thr Ile Ser
                85                  90                  95

Asp Pro Val Gln Leu Glu Val His Met Gly Trp Leu Leu Gln Thr
            100                 105                 110

Thr Lys Trp Leu Phe Gln Glu Gly Asp Pro Ile His Leu Arg Cys His
        115                 120                 125

Ser Trp Gln Asn Arg Pro Val Arg Lys Val Thr Tyr Ser Gln Asn Gly
    130                 135                 140

Lys Gly Lys Lys Tyr Phe His Glu Asn Ser Glu Leu Leu Ile Pro Lys
145                 150                 155                 160

Ala Thr His Asn Asp Ser Gly Ser Tyr Phe Cys Arg Gly Leu Ile Gly
                165                 170                 175

His Asn Asn Lys Ser Ser Ala Ser Phe Arg Ile Ser Leu Gly Asp Pro
            180                 185                 190

Gly Ser Pro Ser Met Phe Pro Pro Trp Tyr Gln Val Ser Phe Cys Leu
        195                 200                 205

Val Met Val Leu Leu Phe Ala Val Asp Thr Gly Leu Tyr Phe Ser Val
    210                 215                 220

Lys Thr Asn Ile Arg Ser Ser Thr Arg Asp Trp Lys Asp His Lys Phe
225                 230                 235                 240

Lys Trp Arg Lys Asp Pro Gln Asp Lys
                245

<210> SEQ ID NO 15
<211> LENGTH: 801
<212> TYPE: DNA
<213> ORGANISM: Artificial
<220> FEATURE:
<223> OTHER INFORMATION: An artificially synthesized nucleotide sequence

<400> SEQUENCE: 15
atgtggcagc tactactacc aacagctctg gtacttacag ctttctctgg cattcaagct      60
ggtctccaaa aggctgtggt gaacctagac cccaagtggg tcagggtgct tgaggaagac     120
agcgtgaccc tcagatgcca aggcactttc tcccccgagg acaattctat caagtggttc     180
cataacgaaa gcctcatccc acaccaggat gccaactatg tcatccaaag tgccagagtt     240
aaggacagtg gaatgtacag gtgccagaca gccctctcca cgatcagtga cccagtgcaa     300
ctagaggtcc atatgggctg gctattgctt cagaccacta gtggctgttc caggagggg      360
gaccccattc atctgagatg ccacagttgg caaaacagac tgtacgaa ggtcacctat       420
tcacagaacg gcaaaggcaa gaagtatttc atgaaaatt ctgaattact cattccaaaa     480
gctacacaca tgacagtgg ctcctacttc tgcagagggc tcattggaca caacaacaaa     540
tcttcagcat cctttcgtat aagcctaggc gatccaggt ctccatccat gtttccaccg      600
tggcctcagc tctgctatat cctggatgcc atcctgtttc tgtatggaat gtcctcacc      660
ctcctctact gtcgactgaa gatccaagtg cgaaaggcag ctataaccag ctatgagaaa     720
tcagatggtg tttacacggg cctgagcacc aggaaccagg agacttacga gactctgaag     780
catgagaaac caccacagta g                                               801

<210> SEQ ID NO 16
<211> LENGTH: 266
<212> TYPE: PRT
<213> ORGANISM: Artificial
<220> FEATURE:
<223> OTHER INFORMATION: An artificially synthesized peptide sequence

<400> SEQUENCE: 16

```
Met Trp Gln Leu Leu Leu Pro Thr Ala Leu Val Leu Thr Ala Phe Ser
1               5                   10                  15

Gly Ile Gln Ala Gly Leu Gln Lys Ala Val Val Asn Leu Asp Pro Lys
            20                  25                  30

Trp Val Arg Val Leu Glu Glu Asp Ser Val Thr Leu Arg Cys Gln Gly
            35                  40                  45

Thr Phe Ser Pro Glu Asp Asn Ser Ile Lys Trp Phe His Asn Glu Ser
        50                  55                  60

Leu Ile Pro His Gln Asp Ala Asn Tyr Val Ile Gln Ser Ala Arg Val
65                  70                  75                  80

Lys Asp Ser Gly Met Tyr Arg Cys Gln Thr Ala Leu Ser Thr Ile Ser
                85                  90                  95

Asp Pro Val Gln Leu Glu Val His Met Gly Trp Leu Leu Leu Gln Thr
            100                 105                 110

Thr Lys Trp Leu Phe Gln Glu Gly Asp Pro Ile His Leu Arg Cys His
            115                 120                 125

Ser Trp Gln Asn Arg Pro Val Arg Lys Val Thr Tyr Ser Gln Asn Gly
        130                 135                 140

Lys Gly Lys Lys Tyr Phe His Glu Asn Ser Glu Leu Leu Ile Pro Lys
145                 150                 155                 160

Ala Thr His Asn Asp Ser Gly Ser Tyr Phe Cys Arg Gly Leu Ile Gly
                165                 170                 175

His Asn Asn Lys Ser Ser Ala Ser Phe Arg Ile Ser Leu Gly Asp Pro
            180                 185                 190

Gly Ser Pro Ser Met Phe Pro Pro Trp Pro Gln Leu Cys Tyr Ile Leu
        195                 200                 205

Asp Ala Ile Leu Phe Leu Tyr Gly Ile Val Leu Thr Leu Leu Tyr Cys
210                 215                 220

Arg Leu Lys Ile Gln Val Arg Lys Ala Ala Ile Thr Ser Tyr Glu Lys
225                 230                 235                 240

Ser Asp Gly Val Tyr Thr Gly Leu Ser Thr Arg Asn Gln Glu Thr Tyr
                245                 250                 255

Glu Thr Leu Lys His Glu Lys Pro Pro Gln
            260                 265

<210> SEQ ID NO 17
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 17
taagaattcc accatgtggc agctactact acc                            33

<210> SEQ ID NO 18
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 18
taagcggccg ctcacttgtc ctgaggttcc                                30

<210> SEQ ID NO 19
<211> LENGTH: 42
<212> TYPE: DNA
```

<213> ORGANISM: Artificial
<220> FEATURE:
<223> OTHER INFORMATION: An artificially synthesized primer sequence

<400> SEQUENCE: 19
taagaattcc caccatgttt cagaatgcac actctggaag cc         42

<210> SEQ ID NO 20
<211> LENGTH: 37
<212> TYPE: DNA
<213> ORGANISM: Artificial
<220> FEATURE:
<223> OTHER INFORMATION: An artificially synthesized primer sequence

<400> SEQUENCE: 20
tttgcggccg ctcacttgtc ttgaggagcc tggtgct              37

<210> SEQ ID NO 21
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 21
gagacttggt accacggtgg aaacatggat g                    31

<210> SEQ ID NO 22
<211> LENGTH: 34
<212> TYPE: DNA
<213> ORGANISM: Artificial
<220> FEATURE:
<223> OTHER INFORMATION: An artificially synthesized primer sequence

<400> SEQUENCE: 22
gtttccaccg tggtaccaag tctctttctg cttg                 34

<210> SEQ ID NO 23
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 23
atgtctgctc gaagcggc                                   18

<210> SEQ ID NO 24
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 24
cagagctgag gccacggtgg aaacatggat g                    31

<210> SEQ ID NO 25
<211> LENGTH: 35
<212> TYPE: DNA
<213> ORGANISM: Artificial
<220> FEATURE:
<223> OTHER INFORMATION: An artificially synthesized primer sequence

<400> SEQUENCE: 25
gtttccaccg tggcctcagc tctgctatat cctgg                35

<210> SEQ ID NO 26
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 26
gcggccgcta ctgtggtggt ttc                                            23

<210> SEQ ID NO 27
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 27
gagacttggt accagactag agagatggag                                     30

<210> SEQ ID NO 28
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 28
ctagtctggt accaagtctc tttctgcttg                                     30

<210> SEQ ID NO 29
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 29
cagagctgag gccagactag agagatggag                                     30

<210> SEQ ID NO 30
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 30
ctagtctggc ctcagctctg ctatatcc                                       28

<210> SEQ ID NO 31
<211> LENGTH: 3000
<212> TYPE: DNA
<213> ORGANISM: Homo sapiens

<400> SEQUENCE: 31 atgatgggc tcttccccag aactacaggg gctctggcca tcttcgtggt ggtcatattg      60
gttcatggag aattgcgaat agagactaaa ggtcaatatg atgaagaaga gatgactatg    120
caacaagcta aagaaggca aaaacgtgaa tgggtgaaat tgccaaaacc ctgcagagaa     180
ggagaagata actcaaaaag aaacccaatt gccaagatta cttcagatta ccaagcaacc    240
cagaaaatca cctaccgaat ctctggagtg ggaatcgatc agccgccttt tggaatcttt    300

```
gttgttgaca aaaacactgg agatattaac ataacagcta tagtcgaccg ggaggaaact    360
ccaagcttcc tgatcacatg tcgggctcta aatgcccaag gactagatgt agagaaacca    420
cttatactaa cggttaaaat tttggatatt aatgataatc ctccagtatt ttcacaacaa    480
attttcatgg gtgaaattga agaaaatagt gcctcaaact cactggtgat gatactaaat    540
gccacagatg cagatgaacc aaaccacttg aattctaaaa ttgccttcaa aattgtctct    600
caggaaccag caggcacacc catgttcctc ctaagcagaa acactgggga agtccgtact    660
ttgaccaatt ctcttgaccg agagcaagct agcagctatc gtctggttgt gagtggtgca    720
gacaaagatg gagaaggact atcaactcaa tgtgaatgta atattaaagt gaaagatgtc    780
aacgataact tcccaatgtt tagagactct cagtattcag cacgtattga agaaaatatt    840
ttaagttctg aattacttcg atttcaagta acagatttgg atgaagagta cacagataat    900
tggcttgcag tatatttctt tacctctggg aatgaaggaa attggtttga aatacaaact    960
gatcctagaa ctaatgaagg catcctgaaa gtggtgaagg ctctagatta tgaacaacta   1020
caaagcgtga aacttagtat tgctgtcaaa aacaaagctg aatttcacca atcagttatc   1080
tctcgatacc gagttcagtc aaccccagtc acaattcagg taataaatgt aagagaagga   1140
attgcattcc gtcctgcttc caagacattt actgtgcaaa aaggcataag tagcaaaaaa   1200
ttggtggatt atatcctggg aacatatcaa gccatcgatg aggacactaa caaagctgcc   1260
tcaaatgtca aatatgtcat gggacgtaac gatggtggat acctaatgat tgattcaaaa   1320
actgctgaaa tcaaatttgt caaaaatatg aaccgagatt ctactttcat agttaacaaa   1380
acaatcacag ctgaggttct ggccatagat gaatacacgg gtaaaacttc tacaggcacg   1440
gtatatgtta gagtacccga tttcaatgac aattgtccaa cagctgtcct cgaaaaagat   1500
gcagtttgca gttcttcacc ttccgtggtt gtctccgcta aacactgaa taatagatac   1560 actggcccct atacatttgc actggaagat caacctgtaa agttgcctgc cgtatggagt   1620
atcacaaccc tcaatgctac ctcggccctc tcagagccc aggaacagat acctcctgga   1680
gtataccaca tctccctggt acttacagac agtcagaaca atcggtgtga gatgccacgc   1740
agcttgacac tggaagtctg tcagtgtgac aacaggggca tctgtggaac ttcttaccca   1800
accacaagcc ctgggaccag gtatggcagg ccgcactcag ggaggctggg gcctgccgcc   1860
atcggcctgc tgctccttgg tctcctgctg ctgctgttgg cccccttct gctgttgacc   1920 tgtgactgtg ggcaggttc tactggggga gtgacaggtg gttttatccc agttcctgat   1980
ggctcagaag gaacaattca tcagtgggga attgaaggag cccatcctga agacaaggaa   2040
atcacaaata tttgtgtgcc tcctgtaaca gccaatggag ccgatttcat ggaaagttct   2100
gaagtttgta caaatacgta tgccagaggc acagcggtgg aaggcacttc aggaatggaa   2160
atgaccacta agcttggagc agccactgaa tctggaggtg ctgcaggctt tgcaacaggg   2220
acagtgtcag gagctgcttc aggattcgga gcagccactg gagttggcat ctgttcctca   2280
gggcagtctg gaaccatgag aacaaggcat tccactggag aaccaataa ggactacgct   2340 gatgggggcga taagcatgaa ttttctggac tcctactttt ctcagaaagc atttgcctgt   2400
gcggaggaag acgatggcca ggaagcaaat gactgcttgt tgatctatga taatgaaggc   2460
gcagatgcca ctggttctcc tgtgggctcc gtgggttgtt gcagttttat tgctgatgac   2520
ctggatgaca gcttcttgga ctcacttgga cccaaattta aaaaacttgc agagataagc   2580
cttggtgttg atggtgaagg caagaagtt cagccacct ctaaagacag cggttatggg   2640
attgaatcct gtggccatcc catagaagtc cagcagacag gatttgttaa gtgccagact   2700
```

-continued

```
ttgtcaggaa gtcaaggagc ttctgctttg tccgcctctg ggtctgtcca gccagctgtt    2760
tccatccctg accctctgca gcatggtaac tatttagtaa cggagactta ctcggcttct    2820
ggttccctcg tgcaaccttc cactgcaggc tttgatccac ttctcacaca aaatgtgata    2880
gtgacagaaa gggtgatctg tcccatttcc agtgttcctg gcaacctagc tggcccaacg    2940
cagctacgag ggtcacatac tatgctctgt acagaggatc cttgctcccg tctaatatga    3000
```

<210> SEQ ID NO 32
<211> LENGTH: 999
<212> TYPE: PRT
<213> ORGANISM: Homo sapiens

<400> SEQUENCE: 32

| Met | Met | Gly | Leu | Phe | Arg | Thr | Thr | Gly | Ala | Leu | Ala | Ile | Phe | Val |
|---|---|---|---|---|---|---|---|---|---|---|---|---|---|---|
| 1 | | | | 5 | | | | | 10 | | | | | 15 |

Val Val Ile Leu Val His Gly Glu Leu Arg Ile Glu Thr Lys Gly Gln
         20                  25                  30

Tyr Asp Glu Glu Glu Met Thr Met Gln Gln Ala Lys Arg Arg Gln Lys
             35                  40                  45

Arg Glu Trp Val Lys Phe Ala Lys Pro Cys Arg Glu Gly Glu Asp Asn
 50                  55                  60

Ser Lys Arg Asn Pro Ile Ala Lys Ile Thr Ser Asp Tyr Gln Ala Thr
 65                  70                  75                  80

Gln Lys Ile Thr Tyr Arg Ile Ser Gly Val Gly Ile Asp Gln Pro Pro
                 85                  90                  95

Phe Gly Ile Phe Val Val Asp Lys Asn Thr Gly Asp Ile Asn Ile Thr
            100                 105                 110

Ala Ile Val Asp Arg Glu Glu Thr Pro Ser Phe Leu Ile Thr Cys Arg
        115                 120                 125

Ala Leu Asn Ala Gln Gly Leu Asp Val Glu Lys Pro Leu Ile Leu Thr
    130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
        195                 200                 205

Phe Leu Leu Ser Arg Asn Thr Gly Glu Val Arg Thr Leu Thr Asn Ser
    210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
        275                 280                 285

Gln Val Thr Asp Leu Asp Glu Glu Tyr Thr Asp Asn Trp Leu Ala Val
    290                 295                 300

Tyr Phe Phe Thr Ser Gly Asn Glu Gly Asn Trp Phe Glu Ile Gln Thr
305                 310                 315                 320

```
Asp Pro Arg Thr Asn Glu Gly Ile Leu Lys Val Val Lys Ala Leu Asp
            325                 330                 335

Tyr Glu Gln Leu Gln Ser Val Lys Leu Ser Ile Ala Val Lys Asn Lys
        340                 345                 350

Ala Glu Phe His Gln Ser Val Ile Ser Arg Tyr Arg Val Gln Ser Thr
            355                 360                 365

Pro Val Thr Ile Gln Val Ile Asn Val Arg Glu Gly Ile Ala Phe Arg
        370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
            420                 425                 430

Gly Tyr Leu Met Ile Asp Ser Lys Thr Ala Glu Ile Lys Phe Val Lys
        435                 440                 445

Asn Met Asn Arg Asp Ser Thr Phe Ile Val Asn Lys Thr Ile Thr Ala
    450                 455                 460

Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
                485                 490                 495

Leu Glu Lys Asp Ala Val Cys Ser Ser Pro Ser Val Val Val Ser
            500                 505                 510

Ala Arg Thr Leu Asn Asn Arg Tyr Thr Gly Pro Tyr Thr Phe Ala Leu
        515                 520                 525

Glu Asp Gln Pro Val Lys Leu Pro Ala Val Trp Ser Ile Thr Thr Leu
    530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
                565                 570                 575

Glu Met Pro Arg Ser Leu Thr Leu Glu Val Cys Gln Cys Asp Asn Arg
        580                 585                 590

Gly Ile Cys Gly Thr Ser Tyr Pro Thr Thr Ser Pro Gly Thr Arg Tyr
    595                 600                 605

Gly Arg Pro His Ser Gly Arg Leu Gly Pro Ala Ala Ile Gly Leu Leu
    610                 615                 620

Leu Leu Gly Leu Leu Leu Leu Leu Ala Pro Leu Leu Leu Thr
625                 630                 635                 640

Cys Asp Cys Gly Ala Gly Ser Thr Gly Gly Val Thr Gly Gly Phe Ile
                645                 650                 655

Pro Val Pro Asp Gly Ser Glu Gly Thr Ile His Gln Trp Gly Ile Glu
        660                 665                 670

Gly Ala His Pro Glu Asp Lys Glu Ile Thr Asn Ile Cys Val Pro Pro
    675                 680                 685

Val Thr Ala Asn Gly Ala Asp Phe Met Glu Ser Glu Val Cys Thr
690                 695                 700

Asn Thr Tyr Ala Arg Gly Thr Ala Val Glu Gly Thr Ser Gly Met Glu
705                 710                 715                 720

Met Thr Thr Lys Leu Gly Ala Ala Thr Glu Ser Gly Ala Ala Gly
                725                 730                 735

Phe Ala Thr Gly Thr Val Ser Gly Ala Ala Ser Gly Phe Gly Ala Ala
```

```
                        740               745                  750
        Thr Gly Val Gly Ile Cys Ser Ser Gly Gln Ser Gly Thr Met Arg Thr
                            755                      760               765

Arg His Ser Thr Gly Gly Thr Asn Lys Asp Tyr Ala Asp Gly Ala Ile
                770                      775                  780

Ser Met Asn Phe Leu Asp Ser Tyr Phe Ser Gln Lys Ala Phe Ala Cys
        785                      790                  795                  800

Ala Glu Glu Asp Asp Gly Gln Glu Ala Asn Asp Cys Leu Leu Ile Tyr
                            805                      810                  815

Asp Asn Glu Gly Ala Asp Ala Thr Gly Ser Pro Val Gly Ser Val Gly
                    820                      825                  830

Cys Cys Ser Phe Ile Ala Asp Leu Asp Asp Ser Phe Leu Asp Ser
                        835                      840                  845

Leu Gly Pro Lys Phe Lys Lys Leu Ala Glu Ile Ser Leu Gly Val Asp
                    850                      855                  860

Gly Glu Gly Lys Glu Val Gln Pro Pro Ser Lys Asp Ser Gly Tyr Gly
        865                      870                  875                  880

Ile Glu Ser Cys Gly His Pro Ile Glu Val Gln Gln Thr Gly Phe Val
                            885                      890                  895

Lys Cys Gln Thr Leu Ser Gly Ser Gln Gly Ala Ser Ala Leu Ser Ala
                        900                      905                  910

Ser Gly Ser Val Gln Pro Ala Val Ser Ile Pro Asp Pro Leu Gln His
                    915                      920                  925

Gly Asn Tyr Leu Val Thr Glu Thr Tyr Ser Ala Ser Gly Ser Leu Val
                    930                      935                  940

Gln Pro Ser Thr Ala Gly Phe Asp Pro Leu Leu Thr Gln Asn Val Ile
        945                      950                  955                  960

Val Thr Glu Arg Val Ile Cys Pro Ile Ser Ser Val Pro Gly Asn Leu
                            965                      970                  975

Ala Gly Pro Thr Gln Leu Arg Gly Ser His Thr Met Leu Cys Thr Glu
                    980                      985                  990

Asp Pro Cys Ser Arg Leu Ile
                    995

<210> SEQ ID NO 33
<211> LENGTH: 2550
<212> TYPE: DNA
<213> ORGANISM: Artificial
<220> FEATURE:
<223> OTHER INFORMATION: An artificially synthesized nucleotide sequence

<400> SEQUENCE: 33
atgatggggc tcttccccag aactacaggg gctctggcca tcttcgtggt ggtcatattg      60
gttcatggag aattgcgaat agagactaaa ggtcaatatg atgaagaaga gatgactatg     120
caacaagcta aagaaggca aaacgtgaa tgggtgaaat tgccaaaacc ctgcagagaa       180
ggagaagata actcaaaaag aaacccaatt gccaagatta cttcagatta ccaagcaacc    240
cagaaaatca cctaccgaat ctctggagtg ggaatcgatc agccgccttt tggaatcttt    300
gttgttgata aaacactgg agatattaac ataacagcta tagtcgaccg ggaggaaact     360
ccaagcttcc tgatcacatg tcgggctcta aatgcccaag actagatgt agagaaacca    420 cttatactaa cggttaaaat tttggatatt aatgataatc ctccagtatt ttcacaacaa    480
attttcatgg gtgaaattga agaaaatagt gcctcaaact cactggtgat gatactaaat    540
gccacagatg cagatgaacc aaaccacttg aactctaaaa ttgccttcaa aattgtctct    600
```

```
caggaaccag caggcacacc catgttcctc ctaagcagaa acactggga agtccgtact      660 ttgaccaatt ctcttgaccg agagcaagct agcagctatc gtctggttgt gagtggtgca      720
gacaaagatg gagaaggact atcaactcaa tgtgaatgta atattaaagt gaaagatgtc      780
aacgataact tcccaatgtt tagagactct cagtattcag cacgtattga agaaaatatt      840
ttaagttctg aattacttcg atttcaagta acagatttgg atgaagagta cacagataat      900
tggcttgcag tatatttctt tacctctggg aatgaaggaa attggtttga aatacaaact      960
gatcctagaa ctaatgaagg catcctgaaa gtggtgaagg ctctagatta tgaacaacta    1020
caaagcgtga aacttagtat tgctgtcaaa acaaagctg aatttcacca atcagttatc     1080
tctcgatacc gagttcagtc aaccccagtc acaattcagg taataaatgt aagagaagga    1140
attgcattcc gtcctgcttc caagacattt actgtgcaaa aaggcataag tagcaaaaaa    1200
ttggtggatt atatcctggg aacatatcaa gccatcgatg aggacactaa caaagctgcc    1260
tcaaatgtca aatatgtcat gggacgtaac gatggtggat acctaatgat tgattcaaaa    1320
actgctgaaa tcaaatttgt caaaaatatg aaccgagatt ctactttcat agttaacaaa    1380
acaatcacag ctgaggttct ggccatagat gaatacacgg gtaaaacttc tacaggcacg    1440
gtatatgtta gagtacccga tttcaatgac aattgtccaa cagctgtcct cgaaaaagat    1500
gcagtttgca gttcttcacc ttccgtggtt gtctccgcta gaacactgaa taatagatac    1560
actggcccct atacatttgc actggaagat caacctgtaa agttgcctgc cgtatggagt    1620
atcacaaccc tcaatgctac ctcggccctc ctcagagccc aggaacagat acctcctgga    1680
gtataccaca tctccctggt acttacagac agtcagaaca tcggtgtga gatgccacgc     1740 agcttgacac tggaagtctg tcagtgtgac aacaggggca tctgtggaac ttcttaccca    1800
accacaagcc ctgggaccag gtatggcagg ccgcactcag ggaggctgga acctcgcgga    1860
ccgacaatca agcccgtcc tccatgcaaa tgcccagcac ctaacctctt gggtggacca     1920
tccgtcttca tcttccctcc aaagatcaag gatgtactca tgatctccct gagccccata    1980
gtcacatgtg tggtggtgga tgtgagcgag gatgacccag atgtccagat cagctggttt    2040
gtgaacaacg tggaagtaca cacagctcag acacaaaccc atagagagga ttacaacagt    2100
actctccggg tggtcagtgc cctccccatc cagcaccagg actggatgag tggcaaggag    2160
ttcaaatgca aggtcaacaa caaagacctc ccagcgccca tcgagagaac catctcaaaa    2220
cccaaagggt cagtaagagc tccacaggta tatgtcttgc ctccaccaga agaagagatg    2280
actaagaaac aggtcactct gacctgcatg gtcacagact tcatgcctga agacatttac    2340
gtggagtgga ccaacaacgg gaaaacagag ctaaactaca agaacactga accagtcctg    2400
gactctgatg gttcttactt catgtacagc aagctgagag tggaaaagaa gaactgggtg    2460
gaaagaaata gctactcctg ttcagtggtc cacgagggtc tgcacaatca ccacgact     2520 aagagcttct cccggactcc gggtaaatga                                     2550
```

<210> SEQ ID NO 34
<211> LENGTH: 849
<212> TYPE: PRT
<213> ORGANISM: Artificial
<220> FEATURE:
<223> OTHER INFORMATION: An artificially synthesized peptide sequence

<400> SEQUENCE: 34

Met Met Gly Leu Phe Pro Arg Thr Thr Gly Ala Leu Ala Ile Phe Val
1               5                   10                  15

```
Val Val Ile Leu Val His Gly Glu Leu Arg Ile Glu Thr Lys Gly Gln
             20                  25                  30

Tyr Asp Glu Glu Glu Met Thr Met Gln Gln Ala Lys Arg Arg Gln Lys
             35                  40                  45

Arg Glu Trp Val Lys Phe Ala Lys Pro Cys Arg Glu Gly Glu Asp Asn
 50                  55                  60

Ser Lys Arg Asn Pro Ile Ala Lys Ile Thr Ser Asp Tyr Gln Ala Thr
 65                  70                  75                  80

Gln Lys Ile Thr Tyr Arg Ile Ser Gly Val Gly Ile Asp Gln Pro Pro
                 85                  90                  95

Phe Gly Ile Phe Val Val Asp Lys Asn Thr Gly Asp Ile Asn Ile Thr
                100                 105                 110

Ala Ile Val Asp Arg Glu Glu Thr Pro Ser Phe Leu Ile Thr Cys Arg
            115                 120                 125

Ala Leu Asn Ala Gln Gly Leu Asp Val Glu Lys Pro Leu Ile Leu Thr
130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
            195                 200                 205

Phe Leu Leu Ser Arg Asn Thr Gly Glu Val Arg Thr Leu Thr Asn Ser
            210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
            275                 280                 285

Gln Val Thr Asp Leu Asp Glu Glu Tyr Thr Asp Asn Trp Leu Ala Val
            290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Lys Ala Leu Asp
                325                 330                 335

Tyr Glu Gln Leu Gln Ser Val Lys Leu Ser Ile Ala Val Lys Asn Lys
            340                 345                 350

Ala Glu Phe His Gln Ser Val Ile Ser Arg Tyr Arg Val Gln Ser Thr
            355                 360                 365

Pro Val Thr Ile Gln Val Ile Asn Val Arg Glu Gly Ile Ala Phe Arg
            370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
            420                 425                 430
```

```
Gly Tyr Leu Met Ile Asp Ser Lys Thr Ala Glu Ile Lys Phe Val Lys
            435                 440                 445

Asn Met Asn Arg Asp Ser Thr Phe Ile Val Asn Lys Thr Ile Thr Ala
450                 455                 460

Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
                    485                 490                 495

Leu Glu Lys Asp Ala Val Cys Ser Ser Pro Ser Val Val Val Ser
                500                 505                 510

Ala Arg Thr Leu Asn Asn Arg Tyr Thr Gly Pro Tyr Thr Phe Ala Leu
            515                 520                 525

Glu Asp Gln Pro Val Lys Leu Pro Ala Val Trp Ser Ile Thr Thr Leu
530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
                565                 570                 575

Glu Met Pro Arg Ser Leu Thr Leu Glu Val Cys Gln Cys Asp Asn Arg
                580                 585                 590

Gly Ile Cys Gly Thr Ser Tyr Pro Thr Thr Ser Pro Gly Thr Arg Tyr
            595                 600                 605

Gly Arg Pro His Ser Gly Arg Leu Glu Pro Arg Gly Pro Thr Ile Lys
            610                 615                 620

Pro Cys Pro Pro Cys Lys Cys Pro Ala Pro Asn Leu Leu Gly Gly Pro
625                 630                 635                 640

Ser Val Phe Ile Phe Pro Pro Lys Ile Lys Asp Val Leu Met Ile Ser
                645                 650                 655

Leu Ser Pro Ile Val Thr Cys Val Val Val Asp Val Ser Glu Asp Asp
                660                 665                 670

Pro Asp Val Gln Ile Ser Trp Phe Val Asn Asn Val Glu Val His Thr
            675                 680                 685

Ala Gln Thr Gln Thr His Arg Glu Asp Tyr Asn Ser Thr Leu Arg Val
690                 695                 700

Val Ser Ala Leu Pro Ile Gln His Gln Asp Trp Met Ser Gly Lys Glu
705                 710                 715                 720

Phe Lys Cys Lys Val Asn Asn Lys Asp Leu Pro Ala Pro Ile Glu Arg
                725                 730                 735

Thr Ile Ser Lys Pro Lys Gly Ser Val Arg Ala Pro Gln Val Tyr Val
            740                 745                 750

Leu Pro Pro Pro Glu Glu Glu Met Thr Lys Lys Gln Val Thr Leu Thr
            755                 760                 765

Cys Met Val Thr Asp Phe Met Pro Glu Asp Ile Tyr Val Glu Trp Thr
770                 775                 780

Asn Asn Gly Lys Thr Glu Leu Asn Tyr Lys Asn Thr Glu Pro Val Leu
785                 790                 795                 800

Asp Ser Asp Gly Ser Tyr Phe Met Tyr Ser Lys Leu Arg Val Glu Lys
                805                 810                 815

Lys Asn Trp Val Glu Arg Asn Ser Tyr Ser Cys Ser Val Val His Glu
                820                 825                 830

Gly Leu His Asn His His Thr Thr Lys Ser Phe Ser Arg Thr Pro Gly
            835                 840                 845

Lys
```

<210> SEQ ID NO 35
<211> LENGTH: 426
<212> TYPE: DNA
<213> ORGANISM: Mus musculus

<400> SEQUENCE: 35

```
atgggatgga actggatctt tctcttcctc ctgtcaggaa ctgcaggtgt cctctctgag      60
gtccagctgc agcagtctgg acctgaactg gtgaagcctg ggcttcagt gaagatatcc     120
tgcaaggctt ctggatacac attcactgac tacaacatgg actgggtgaa gcagagccat    180
ggagagagcc ttgagtggat tggatatatt tatcctaaca atggtggttc tggctacaac    240
cagaagttca agagcaaggc cacattgact gtagacaagt cctccagcac agcctacatg    300
gagctccaca gcctgacatc tgaagactct gcagtctatt actgtgcaag acgggatagt    360
tactatggtt tcgacatggc ctggtttgct tactggggcc aagggactct ggtcactgtc    420
tctgca                                                                426
```

<210> SEQ ID NO 36
<211> LENGTH: 142
<212> TYPE: PRT
<213> ORGANISM: Mus musculus

<400> SEQUENCE: 36

```
Met Gly Trp Asn Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Glu Ser Leu
    50                  55                  60

Glu Trp Ile Gly Tyr Ile Tyr Pro Asn Asn Gly Gly Ser Gly Tyr Asn
65                  70                  75                  80

Gln Lys Phe Lys Ser Lys Ala Thr Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Arg Asp Ser Tyr Tyr Gly Phe Asp Met Ala Trp
        115                 120                 125

Phe Ala Tyr Trp Gly Gln Gly Thr Leu Val Thr Val Ser Ala
    130                 135                 140
```

<210> SEQ ID NO 37
<211> LENGTH: 381
<212> TYPE: DNA
<213> ORGANISM: Mus musculus

<400> SEQUENCE: 37

```
atgagtgtgc ccactcaggt cctggggttg ctgctgctgt ggcttacagg tgccagatgt      60
gacatccaga tgactcagtc tccagcctcc tatctgcat ctgtgggaga aactgtcacc     120
atcacatgtc gaccaagtga gaatatttac aataatttag catggtatca acagaaacag    180
ggaaaatctc ctcagctcct ggtctatgtt gcaacaaatt tagcagaagg tgtgccatca    240
aggttcagtg gcagtggatc aggcacacgg ttttctctga agatcaacag cctgcagcct    300
gaagattttg ggaagtatta ctgtcaacat tcttatggta ctccgtggac gttcggtgga    360
```
ggcaccaagc tggagatcaa a                                              381

<210> SEQ ID NO 38
<211> LENGTH: 127
<212> TYPE: PRT
<213> ORGANISM: Mus musculus

<400> SEQUENCE: 38

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Pro Ser Glu Asn
        35                  40                  45

Ile Tyr Asn Asn Leu Ala Trp Tyr Gln Gln Lys Gln Gly Lys Ser Pro
    50                  55                  60

Gln Leu Leu Val Tyr Val Ala Thr Asn Leu Ala Glu Gly Val Pro Ser
65                  70                  75                  80

Arg Phe Ser Gly Ser Gly Ser Gly Thr Arg Phe Ser Leu Lys Ile Asn
                85                  90                  95

Ser Leu Gln Pro Glu Asp Phe Gly Lys Tyr Tyr Cys Gln His Ser Tyr
            100                 105                 110

Gly Thr Pro Trp Thr Phe Gly Gly Gly Thr Lys Leu Glu Ile Lys
        115                 120                 125

<210> SEQ ID NO 39
<211> LENGTH: 1004
<212> TYPE: DNA
<213> ORGANISM: Homo sapiens

<400> SEQUENCE: 39
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tgataagcgg ccgc                    1004

<210> SEQ ID NO 40

```
<211> LENGTH: 330
<212> TYPE: PRT
<213> ORGANISM: Homo sapiens

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 335
<212> TYPE: DNA
<213> ORGANISM: Homo sapiens

<400> SEQUENCE: 41
cgtacggtgg ctgcaccatc tgtcttcatc ttcccgccat ctgatgagca gttgaaatct    60
```

```
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttgataagcg gccgc                               335
```

<210> SEQ ID NO 42
<211> LENGTH: 107
<212> TYPE: PRT
<213> ORGANISM: Homo sapiens

<400> SEQUENCE: 42

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 43
<211> LENGTH: 1416
<212> TYPE: DNA
<213> ORGANISM: Artificial
<220> FEATURE:
<223> OTHER INFORMATION: An artificially synthesized nucleotide sequence

<400> SEQUENCE: 43

```
atgggatgga actggatctt tctcttcctc ctgtcaggaa ctgcaggtgt cctctctgag     60
gtccagctgc agcagtctgg acctgaactg gtgaagcctg gggcttcagt gaagatatcc    120
tgcaaggctt ctggatacac attcactgac tacaacatgg actgggtgaa gcagagccat    180
ggagagagcc ttgagtggat tggatatatt tatcctaaca atggtggttc tggctacaac    240
cagaagttca gagcaaggc cacattgact gtagacaagt cctccagcac agcctacatg    300
gagctccaca gcctgacatc tgaagactct gcagtctatt actgtgcaag acgggatagt    360
tactatggtt tcgacatggc ctggtttgct tactgggga agggactct ggtcactgtc    420 tctgcagcta gcaccaaggg cccatcggtc ttccccctgg cacctccc caagagcacc    480 tctgggggca gcggcgccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840 accccctgagg tcacatgcgt ggtggtggac gtgagccacg aagaccctga ggtcaagttc    900
```

```
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416
```

<210> SEQ ID NO 44
<211> LENGTH: 472
<212> TYPE: PRT
<213> ORGANISM: Artificial
<220> FEATURE:
<223> OTHER INFORMATION: An artificially synthesized peptide sequence

<400> SEQUENCE: 44

```
Met Gly Trp Asn Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Glu Ser Leu
    50                  55                  60

Glu Trp Ile Gly Tyr Ile Tyr Pro Asn Gly Gly Ser Gly Tyr Asn
65                  70                  75                  80

Gln Lys Phe Lys Ser Lys Ala Thr Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Arg Asp Ser Tyr Tyr Gly Phe Asp Met Ala Trp
        115                 120                 125

Phe Ala Tyr Trp Gly Gln Gly Thr Leu Val Thr Val Ser Ala Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270
```

```
Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
                385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 45
<211> LENGTH: 702
<212> TYPE: DNA
<213> ORGANISM: Artificial
<220> FEATURE:
<223> OTHER INFORMATION: An artificially synthesized nucleotide sequence

<400> SEQUENCE: 45
atgagtgtgc ccactcaggt cctggggttg ctgctgctgt ggcttacagg tgccagatgt     60
gacatccaga tgactcagtc tccagcctcc ctatctgcat ctgtgggaga aactgtcacc    120
atcacatgtc gaccaagtga gaatatttac aataatttag catggtatca acagaaacag    180
ggaaaatctc ctcagctcct ggtctatgtt gcaacaaatt tagcagaagg tgtgccatca    240
aggttcagtg gcagtggatc aggcacacgg ttttctctga agatcaacag cctgcagcct    300
gaagattttg ggagtattac tgtcaacat tcttatggta ctccgtggac gttcggtgga    360
ggcaccaagc tggagatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                       702

<210> SEQ ID NO 46
<211> LENGTH: 234
<212> TYPE: PRT
<213> ORGANISM: Artificial
<220> FEATURE:
```

<223> OTHER INFORMATION: An artificially synthesized peptide sequence

<400> SEQUENCE: 46

```
Met Ser Val Pro Thr Gln Val Leu Gly Leu Leu Leu Trp Leu Thr
 1               5                  10                  15
Gly Ala Arg Cys Asp Ile Gln Met Thr Gln Ser Pro Ala Ser Leu Ser
            20                  25                  30
Ala Ser Val Gly Glu Thr Val Thr Ile Thr Cys Arg Pro Ser Glu Asn
        35                  40                  45
Ile Tyr Asn Asn Leu Ala Trp Tyr Gln Gln Lys Gln Gly Lys Ser Pro
    50                  55                  60
Gln Leu Leu Val Tyr Val Ala Thr Asn Leu Ala Glu Gly Val Pro Ser
65                  70                  75                  80
Arg Phe Ser Gly Ser Gly Ser Gly Thr Arg Phe Ser Leu Lys Ile Asn
                85                  90                  95
Ser Leu Gln Pro Glu Asp Phe Gly Lys Tyr Tyr Cys Gln His Ser Tyr
            100                 105                 110
Gly Thr Pro Trp Thr Phe Gly Gly Gly Thr Lys Leu Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 47
<211> LENGTH: 1006
<212> TYPE: DNA
<213> ORGANISM: Mus musculus

<400> SEQUENCE: 47

```
tcgcgaaaac aacagcccca tcggtctatc cactggcccc tgtgtgtgga gatacaactg      60
gctcctcggt gactctagga tgcctggtca agggttattt ccctgagcca gtgaccttga     120
cctggaactc tggatccctg tccagtggtg tgcacacctt cccagctgtc ctgcagtctg     180
acctctacac cctcagcagc tcagtgactg taacctcgag cacctggccc agccagtcca     240
tcacctgcaa tgtggcccac ccggcaagca gcaccaaggt ggacaagaaa attgagccca     300
gagggcccac aatcaagccc tgtcctccat gcaaatgccc agcacctaac ctcttgggtg     360
gaccatccgt cttcatcttc cctccaaaga tcaaggatgt actcatgatc tccctgagcc     420
ccatagtcac atgtgtggtg gtggatgtga gcgaggatga cccagatgtc cagatcagct     480
ggtttgtgaa caacgtggaa gtacacacag ctcagacaca aacccataga gaggattaca     540
acagtactct ccgggtggtc agtgccctcc ccatccagca ccaggactgg atgagtggca     600
aggagttcaa atgcaaggtc aacaacaaag acctcccagc gcccatcgag agaaccatct     660
```

-continued

```
caaaacccaa agggtcagta agagcaccac aggtatatgt cttgcctcca ccagaagaag    720
agatgactaa gaaacaggtc actctgacct gcatggtcac agacttcatg cctgaagaca    780
tttacgtgga gtggaccaac aacgggaaaa cagagctaaa ctacaagaac actgaaccag    840
tcctggactc tgatggttct tacttcatgt acagcaagct gagagtggaa agaagaact    900 gggtggaaag aaatagctac tcctgttcag tggtccacga gggtctgcac aatcaccaca    960
cgactaagag cttctcccgg actccgggta aatgataagc ggccgc                  1006
```

<210> SEQ ID NO 48
<211> LENGTH: 330
<212> TYPE: PRT
<213> ORGANISM: Mus musculus

<400> SEQUENCE: 48

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320
```

```
<210> SEQ ID NO 49
<211> LENGTH: 333
<212> TYPE: DNA
<213> ORGANISM: Mus musculus

<400> SEQUENCE: 49
tcgcgatgcg gccccaactg tatccatctt cccaccatcc agtgagcagt taacatctgg      60
aggtgcctca gtcgtgtgct tcttgaacaa cttctacccc aaagacatca atgtcaagtg     120
gaagattgat ggcagtgaac gacaaaatgg cgtcctgaac agttggactg atcaggacag     180
caaagacagc acctacagca tgagcagcac cctcacgttg accaaggacg agtatgaacg     240
acataacagc tatacctgtg aggccactca caagacatca acttcaccca ttgtcaagag     300
cttcaacagg aatgagtgtt gataagcggc cgc                                  333

<210> SEQ ID NO 50
<211> LENGTH: 107
<212> TYPE: PRT
<213> ORGANISM: Mus musculus

<400> SEQUENCE: 50
```

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

```
<210> SEQ ID NO 51
<211> LENGTH: 1430
<212> TYPE: DNA
<213> ORGANISM: Artificial
<220> FEATURE:
<223> OTHER INFORMATION: An artificially synthesized nucleotide sequence

<400> SEQUENCE: 51
atgggatgga actggatctt tctcttcctc ctgtcaggaa ctgcaggtgt cctctctgag      60
gtccagctgc agcagtctgg acctgaactg gtgaagcctg gggcttcagt gaagatatcc     120
tgcaaggctt ctggatacac attcactgac tacaacatgg actgggtgaa gcagagccat     180
ggagagagcc ttagtggat tgatatatat tatcctaaca atggtggttc tggctacaac     240
cagaagttca gagcaaggc cacattgact gtagacaagt cctccagcac agcctacatg     300
gagctccaca gcctgacatc tgaagactct gcagtctatt actgtgcaag acgggatagt     360
tactatggtt tcgacatggc ctggtttgct tactgggggcc aagggactct ggtcactgtc     420
tctgcagcga aaacaacagc cccatcggtc tatccactgg cccctgtgtg tggagataca     480
```

-continued

```
actggctcct cggtgactct aggatgcctg gtcaagggtt atttccctga gccagtgacc      540
ttgacctgga actctggatc cctgtccagt ggtgtgcaca ccttcccagc tgtcctgcag      600
tctgacctct acaccctcag cagctcagtg actgtaacct cgagcacctg gcccagccag      660
tccatcacct gcaatgtggc ccacccggca agcagcacca aggtggacaa gaaaattgag      720
cccagagggc ccacaatcaa gccctgtcct ccatgcaaat gcccagcacc taacctcttg      780
ggtggaccat ccgtcttcat cttccctcca aagatcaagg atgtactcat gatctccctg      840
agccccatag tcacatgtgt ggtggtggat gtgagcgagg atgacccaga tgtccagatc      900
agctggtttg tgaacaacgt ggaagtacac acagctcaga cacaaaccca tagagaggat      960
tacaacagta ctctccgggt ggtcagtgcc ctccccatcc agcaccagga ctggatgagt     1020
ggcaaggagt tcaaatgcaa ggtcaacaac aaagacctcc cagcgcccat cgagagaacc     1080
atctcaaaac ccaagggtc agtaagagca ccacaggtat atgtcttgcc tccaccagaa     1140
gaagagatga ctaagaaaca ggtcactctg acctgcatgg tcacagactt catgcctgaa     1200
gacatttacg tggagtggac caacaacggg aaaacagagc taaactacaa gaacactgaa     1260
ccagtcctgg actctgatgg ttcttacttc atgtacagca agctgagagt ggaaaagaag     1320
aactgggtgg aaagaaatag ctactcctgt tcagtggtcc acgagggtct gcacaatcac     1380
cacacgacta agagcttctc ccggactccg ggtaaatgat aagcggccgc               1430
```

<210> SEQ ID NO 52
<211> LENGTH: 472
<212> TYPE: PRT
<213> ORGANISM: Artificial
<220> FEATURE:
<223> OTHER INFORMATION: An artificially synthesized peptide sequence

<400> SEQUENCE: 52

```
Met Gly Trp Asn Trp Ile Phe Leu Phe Leu Leu Ser Gly Thr Ala Gly
  1               5                  10                  15

Val Leu Ser Glu Val Gln Leu Gln Gln Ser Gly Pro Glu Leu Val Lys
             20                  25                  30

Pro Gly Ala Ser Val Lys Ile Ser Cys Lys Ala Ser Gly Tyr Thr Phe
         35                  40                  45

Thr Asp Tyr Asn Met Asp Trp Val Lys Gln Ser His Gly Glu Ser Leu
     50                  55                  60

Glu Trp Ile Gly Tyr Ile Tyr Pro Asn Asn Gly Ser Gly Tyr Asn
 65                  70                  75                  80

Gln Lys Phe Lys Ser Lys Ala Thr Leu Thr Val Asp Lys Ser Ser
                 85                  90                  95

Thr Ala Tyr Met Glu Leu His Ser Leu Thr Ser Glu Asp Ser Ala Val
            100                 105                 110

Tyr Tyr Cys Ala Arg Arg Asp Ser Tyr Tyr Gly Phe Asp Met Ala Trp
        115                 120                 125

Phe Ala Tyr Trp Gly Gln Gly Thr Leu Val Thr Val Ser Ala Ala Lys
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Gly Val
            180                 185                 190

His Thr Phe Pro Ala Val Leu Gln Ser Asp Leu Tyr Thr Leu Ser Ser
```

```
                195                 200                 205
Ser Val Thr Val Thr Ser Ser Thr Trp Pro Ser Gln Ser Ile Thr Cys
    210                 215                 220
Asn Val Ala His Pro Ala Ser Ser Thr Lys Val Asp Lys Lys Ile Glu
225                 230                 235                 240
Pro Arg Gly Pro Thr Ile Lys Pro Cys Pro Pro Cys Lys Cys Pro Ala
                245                 250                 255
Pro Asn Leu Leu Gly Gly Pro Ser Val Phe Ile Phe Pro Pro Lys Ile
            260                 265                 270
Lys Asp Val Leu Met Ile Ser Leu Ser Pro Ile Val Thr Cys Val Val
        275                 280                 285
Val Asp Val Ser Glu Asp Asp Pro Asp Val Gln Ile Ser Trp Phe Val
290                 295                 300
Asn Asn Val Glu Val His Thr Ala Gln Thr Gln Thr His Arg Glu Asp
305                 310                 315                 320
Tyr Asn Ser Thr Leu Arg Val Val Ser Ala Leu Pro Ile Gln His Gln
                325                 330                 335
Asp Trp Met Ser Gly Lys Glu Phe Lys Cys Lys Val Asn Asn Lys Asp
            340                 345                 350
Leu Pro Ala Pro Ile Glu Arg Thr Ile Ser Lys Pro Lys Gly Ser Val
        355                 360                 365
Arg Ala Pro Gln Val Tyr Val Leu Pro Pro Pro Glu Glu Glu Met Thr
370                 375                 380
Lys Lys Gln Val Thr Leu Thr Cys Met Val Thr Asp Phe Met Pro Glu
385                 390                 395                 400
Asp Ile Tyr Val Glu Trp Thr Asn Asn Gly Lys Thr Glu Leu Asn Tyr
                405                 410                 415
Lys Asn Thr Glu Pro Val Leu Asp Ser Asp Gly Ser Tyr Phe Met Tyr
            420                 425                 430
Ser Lys Leu Arg Val Glu Lys Lys Asn Trp Val Glu Arg Asn Ser Tyr
        435                 440                 445
Ser Cys Ser Val Val His Glu Gly Leu His Asn His His Thr Thr Lys
    450                 455                 460
Ser Phe Ser Arg Thr Pro Gly Lys
465                 470

<210> SEQ ID NO 53
<211> LENGTH: 716
<212> TYPE: DNA
<213> ORGANISM: Artificial
<220> FEATURE:
<223> OTHER INFORMATION: An artificially synthesized nucleotide sequence

<400> SEQUENCE: 53
atgagtgtgc ccactcaggt cctggggttg ctgctgctgt ggcttacagg tgccagatgt     60
gacatccaga tgactcagtc tccagcctcc ctatctgcat ctgtgggaga aactgtcacc    120
atcacatgtc gaccaagtga gaatatttac aataatttag catggtatca acagaaacag    180
ggaaaatctc ctcagctcct ggtctatgtt gcaacaaatt tagcagaagg tgtgccatca    240
aggttcagtg gcagtggatc aggcacacgg ttttctctga gatcaacag cctgcagcct    300 gaagattttg ggagtattac tgtcaacat tcttatggta ctccgtggac gttcggtgga    360
ggcaccaagc tggagatcaa acgggccgat gcggccccaa ctgtatccat cttcccacca    420
tccagtgagc agttaacatc tggaggtgcc tcagtcgtgt gcttcttgaa caacttctac    480
```

```
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttgataagc ggccgc       716
```

<210> SEQ ID NO 54
<211> LENGTH: 234
<212> TYPE: PRT
<213> ORGANISM: Artificial
<220> FEATURE:
<223> OTHER INFORMATION: An artificially synthesized peptide sequence

<400> SEQUENCE: 54

```
Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Pro Ser Glu Asn
            35                  40                  45

Ile Tyr Asn Asn Leu Ala Trp Tyr Gln Gln Lys Gln Gly Lys Ser Pro
50                  55                  60

Gln Leu Leu Val Tyr Val Ala Thr Asn Leu Ala Glu Gly Val Pro Ser
65                  70                  75                  80

Arg Phe Ser Gly Ser Gly Ser Gly Thr Arg Phe Ser Leu Lys Ile Asn
                85                  90                  95

Ser Leu Gln Pro Glu Asp Phe Gly Lys Tyr Tyr Cys Gln His Ser Tyr
            100                 105                 110

Gly Thr Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230
```

<210> SEQ ID NO 55
<211> LENGTH: 120
<212> TYPE: PRT
<213> ORGANISM: Mus musculus

<400> SEQUENCE: 55

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45
```

Gly Arg Val Asn Pro Ser Asn Gly Gly Thr Ser Tyr Asn Gln Lys Phe
            50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Ala Tyr Tyr Ser Asn Ser Phe Val Tyr Trp Gly Gln
            100                 105                 110

Gly Thr Leu Val Thr Val Ser Ala
            115                 120

<210> SEQ ID NO 56
<211> LENGTH: 112
<212> TYPE: PRT
<213> ORGANISM: Mus musculus

<400> SEQUENCE: 56

Lys Ile Val Leu Thr Gln Ser Pro Ala Ser Leu Ala Val Ser Leu Arg
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
            100                 105                 110

<210> SEQ ID NO 57
<211> LENGTH: 117
<212> TYPE: PRT
<213> ORGANISM: Mus musculus

<400> SEQUENCE: 57

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Val Tyr Tyr Cys
                85                  90                  95

Ala Arg Ser Gly Asp Trp Tyr Phe Asp Val Trp Gly Ala Gly Thr Thr
            100                 105                 110

Val Thr Val Ser Ser
            115

<210> SEQ ID NO 58

<211> LENGTH: 112
<212> TYPE: PRT
<213> ORGANISM: Mus musculus

<400> SEQUENCE: 58

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Phe Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Arg Thr Phe Gly Gly Gly Thr Lys Leu Glu Ile Lys Arg
            100                 105                 110

<210> SEQ ID NO 59
<211> LENGTH: 120
<212> TYPE: PRT
<213> ORGANISM: Mus musculus

<400> SEQUENCE: 59

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Ala Tyr Tyr Ser Asn Ser Phe Thr Tyr Trp Gly Gln
            100                 105                 110

Gly Thr Leu Val Thr Val Ser Ala
        115                 120

<210> SEQ ID NO 60
<211> LENGTH: 112
<212> TYPE: PRT
<213> ORGANISM: Mus musculus

<400> SEQUENCE: 60

Lys Ile Val Leu Thr Gln Ser Pro Ala Ser Leu Ala Val Ser Leu Arg
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

-continued

```
Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
            100                 105                 110
```